(12) United States Patent
Vollmer et al.

(10) Patent No.: US 7,446,880 B2
(45) Date of Patent: Nov. 4, 2008

(54) METHOD AND APPARATUS FOR MEASURING AND MONITORING OPTICAL PROPERTIES BASED ON A RING-RESONATOR

(75) Inventors: Frank Vollmer, Boston, MA (US); Peer Fischer, Belmont, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/398,608

(22) Filed: Apr. 6, 2006

(65) Prior Publication Data
US 2006/0227331 A1    Oct. 12, 2006

Related U.S. Application Data

(60) Provisional application No. 60/668,784, filed on Apr. 6, 2005, provisional application No. 60/705,002, filed on Aug. 3, 2005.

(51) Int. Cl.
*G01B 9/02* (2006.01)
(52) U.S. Cl. ........................... 356/480; 356/519
(58) Field of Classification Search ............... 356/480, 356/519
See application file for complete search history.

(56) References Cited

U.S. PATENT DOCUMENTS

| | | | | |
|---|---|---|---|---|
| 4,995,697 | A * | 2/1991 | Adamovsky | 356/480 |
| 5,009,505 | A * | 4/1991 | Malvern | 356/480 |
| 5,231,611 | A * | 7/1993 | Laznicka, Jr. | 356/480 |
| 5,538,850 | A * | 7/1996 | King et al. | 356/519 |
| 5,663,790 | A * | 9/1997 | Ekstrom et al. | 356/481 |
| 6,490,039 | B2 | 12/2002 | Maleki et al. | |
| 6,721,053 | B1 * | 4/2004 | Maseeh | 385/12 |
| 6,842,548 | B2 | 1/2005 | Loock et al. | |
| 6,901,101 | B2 | 5/2005 | Frick | |
| 7,019,847 | B1 * | 3/2006 | Bearman et al. | 356/480 |
| 7,123,800 | B2 * | 10/2006 | Kaplan | 385/50 |
| 2002/0140946 | A1 | 10/2002 | Groot | |
| 2003/0098971 | A1 | 5/2003 | Laffont | |
| 2004/0023396 | A1 | 2/2004 | Boyd | |

FOREIGN PATENT DOCUMENTS

JP         410246694 A  *  9/1998

OTHER PUBLICATIONS

H. Okamura and K. Iwatsuki, "A Finesse-Enhanced Er-Doped-Fiber Ring Resonator," Journal of Lightwave Technology, vol. 9, No.11 (Nov. 1991).

* cited by examiner

*Primary Examiner*—Samuel A Turner
(74) *Attorney, Agent, or Firm*—24IP Law Group USA; Timothy R. DeWitt

(57) ABSTRACT

A method and apparatus for performing refractive index, birefringence and optical activity measurements of a material such as a solid, liquid, gas or thin film. The apparatus has an optical ring-resonator with a closed optical path that constitutes a cavity. A sample is introduced into the optical path of the resonator such that the light in the resonator is transmitted through the sample and relative and/or absolute shifts of the resonance frequencies or changes of the characteristics of the transmission spectrum are observed. A change in the transfer characteristics of the resonant ring, such as a shift of the resonance frequency, is related to a sample's refractive index (refractive indices) and/or change thereof. A reflecting surface may be introduced in a ring resonator. The reflecting surface can be raster-scanned for the purpose of height-profiling surface features.

24 Claims, 38 Drawing Sheets

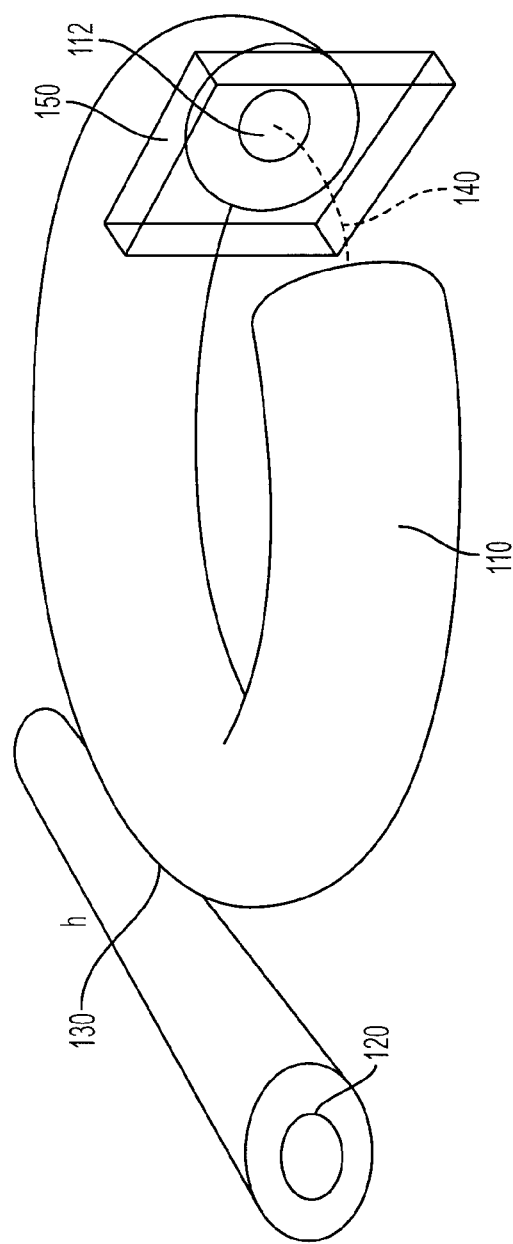
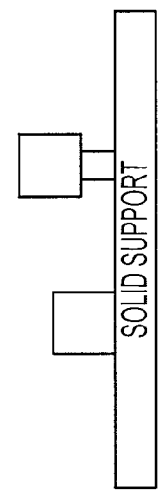
FIG. 1(a)
FIG. 1(b)
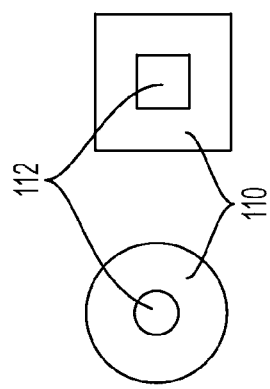
FIG. 1(c)

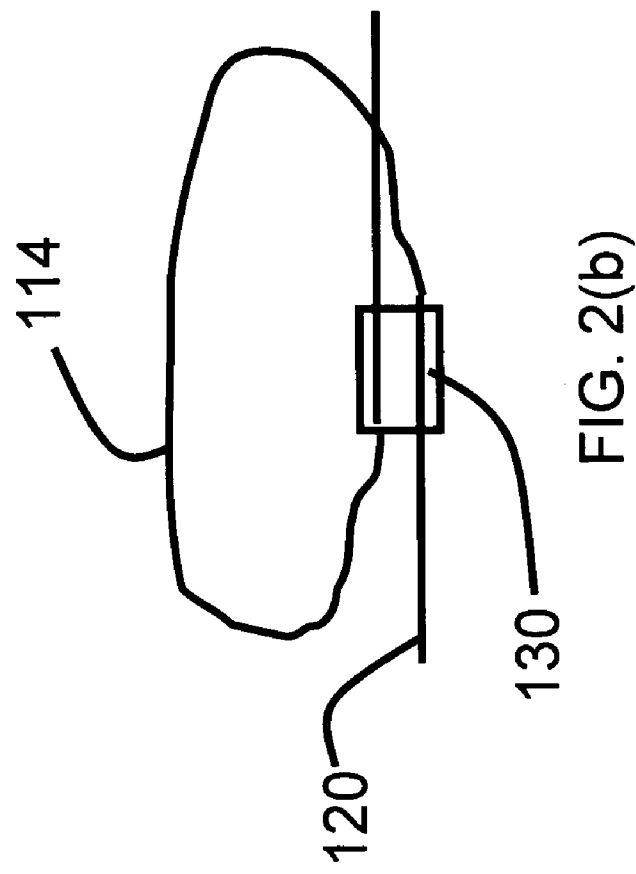
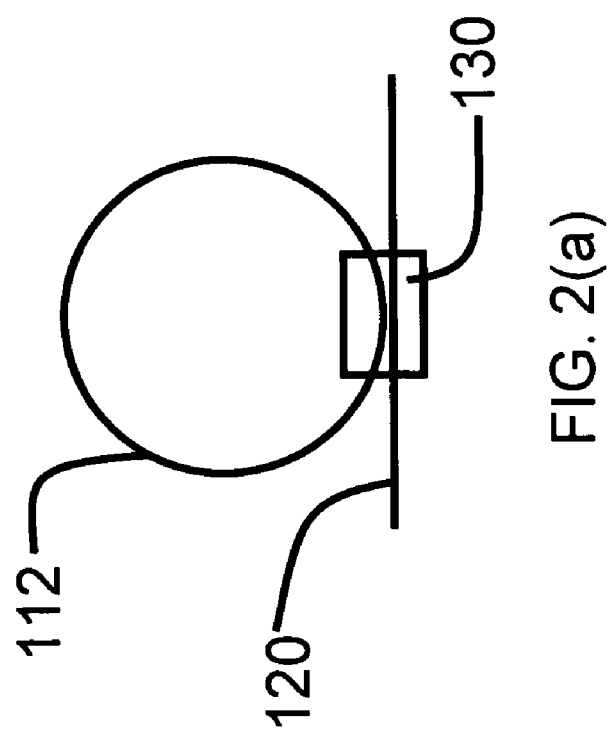

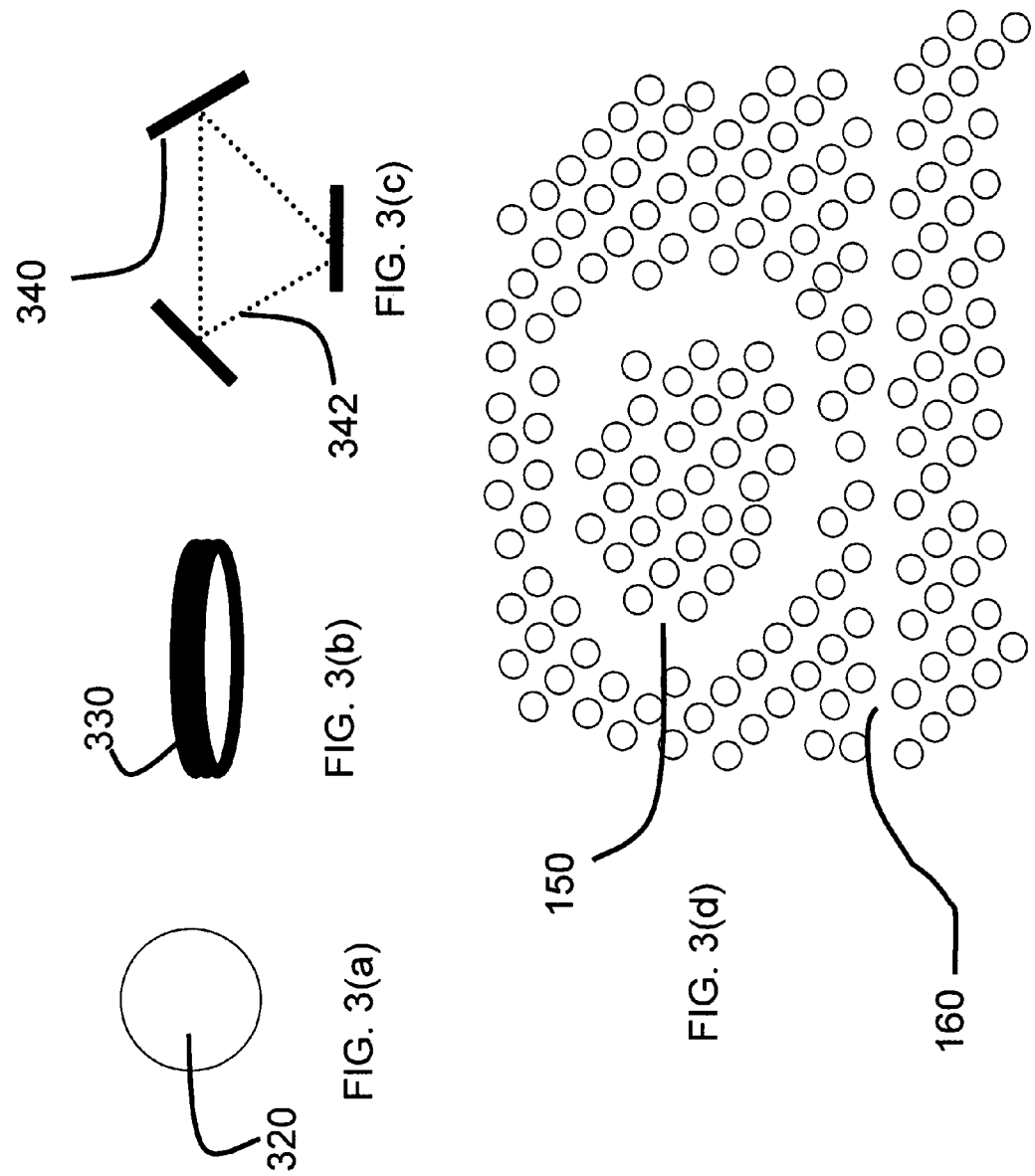

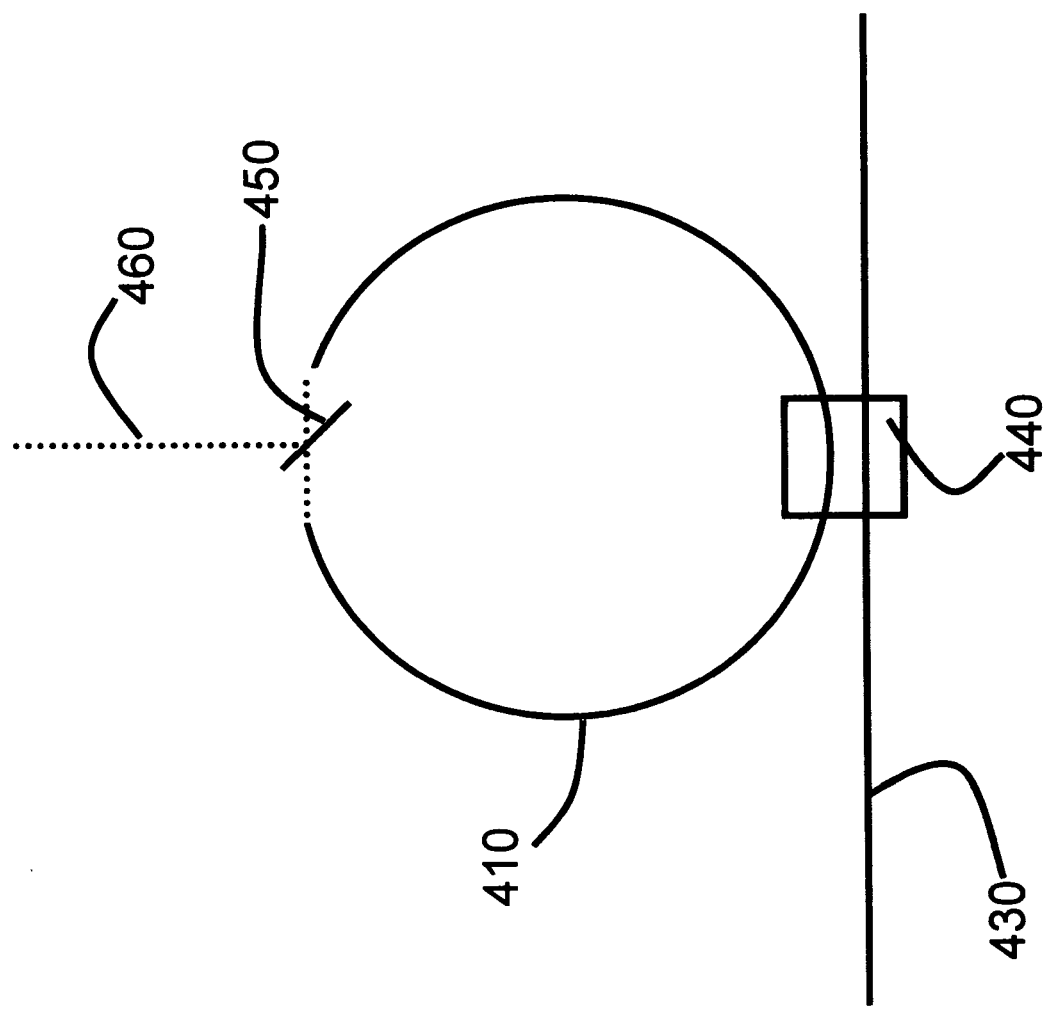

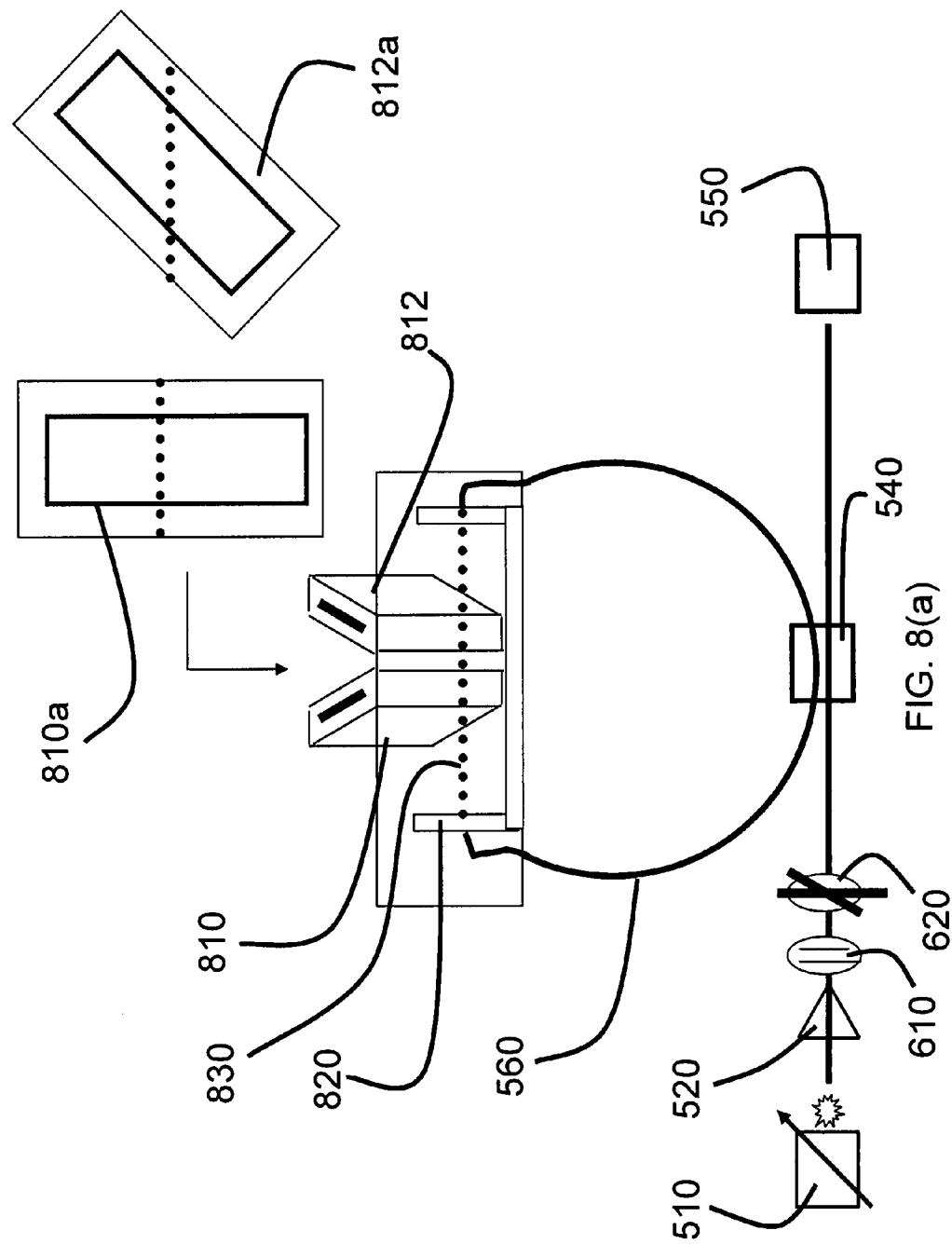

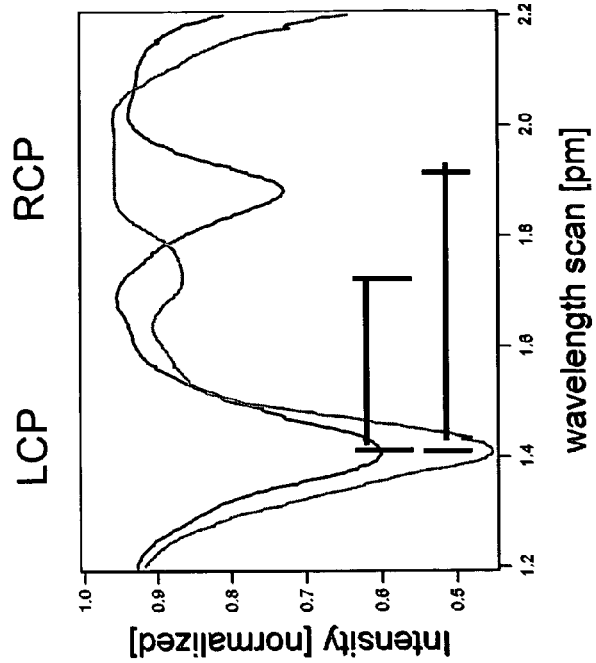
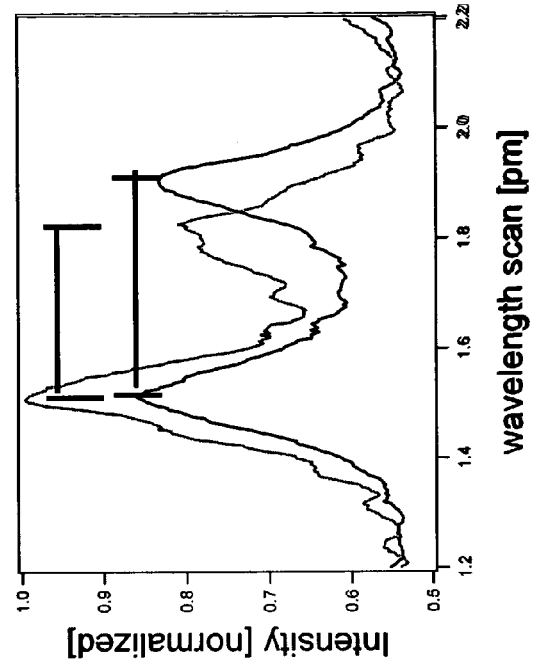
Fig. 11a
Fig. 11b

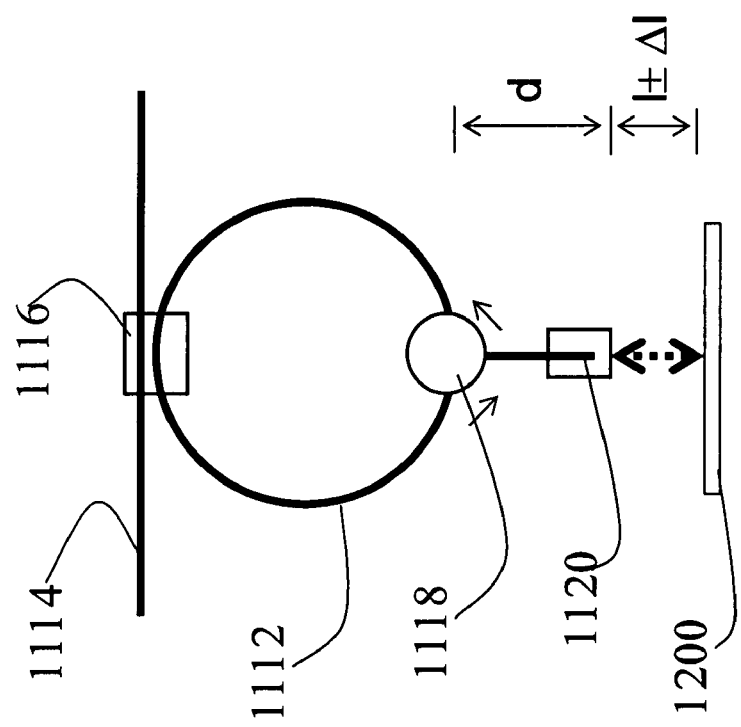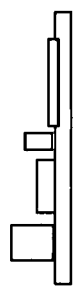

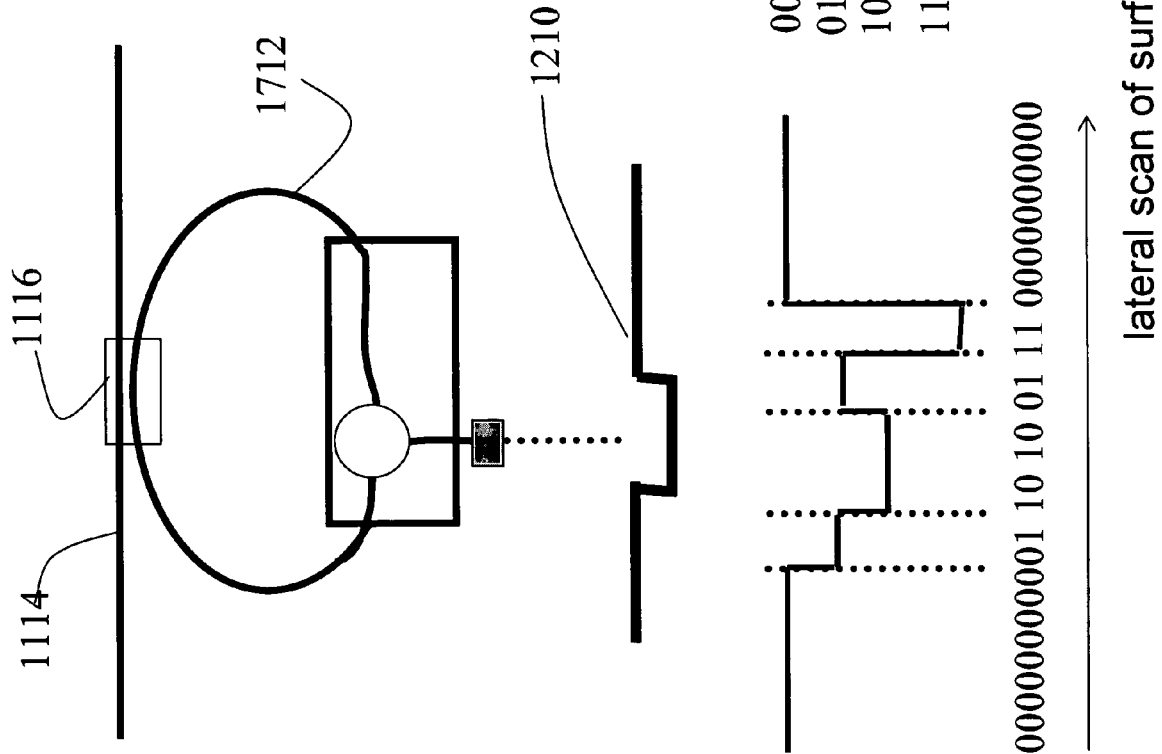

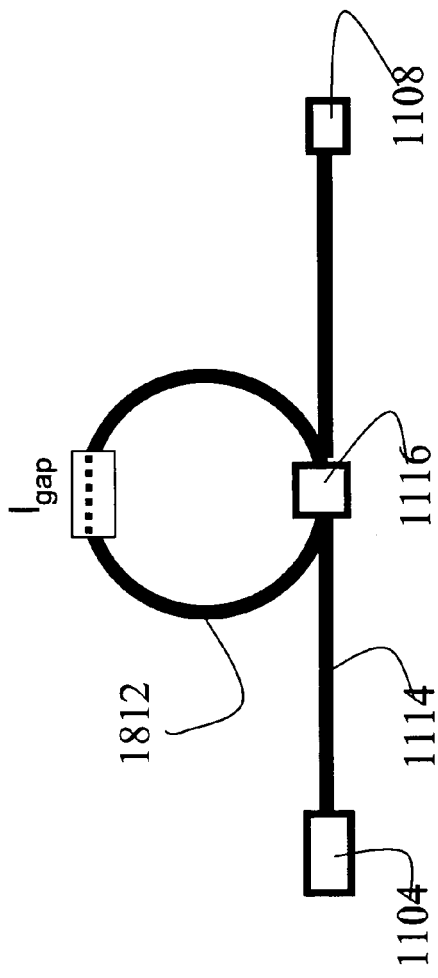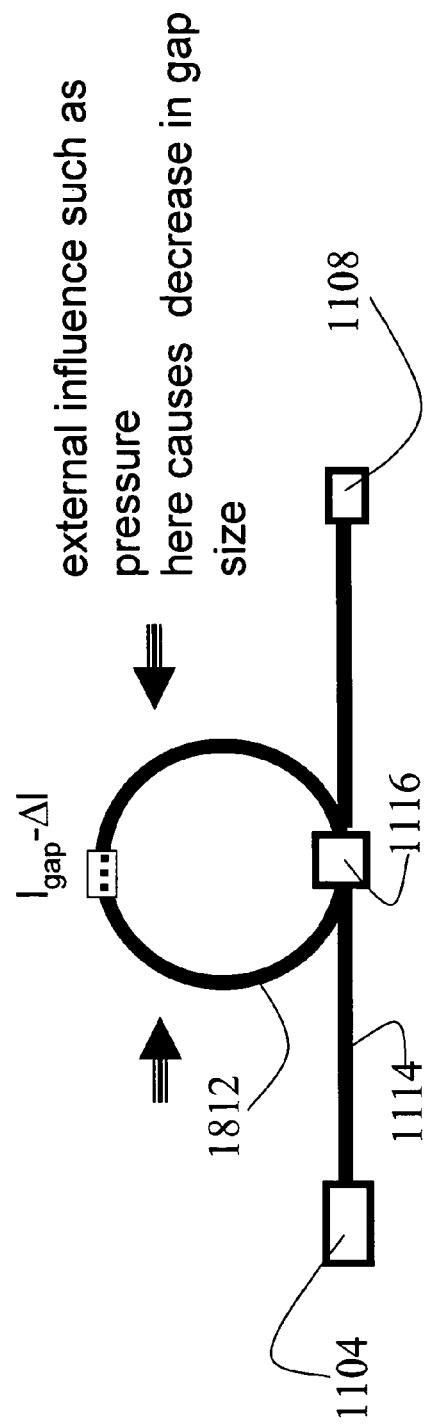

METHOD AND APPARATUS FOR MEASURING AND MONITORING OPTICAL PROPERTIES BASED ON A RING-RESONATOR

CROSS-REFERENCE TO RELATED APPLICATIONS

The present application claims the benefit of the filing dates of U.S. Provisional Application Ser. No. 60/668,784 entitled "Method and Apparatus for Measuring Optical Properties," and filed on Apr. 6, 2005 and U.S. Provisional Application Ser. No. 60/705,002 entitled "Method And Apparatus For Measuring And Monitoring Distances And Physical Properties As Well As Phase Changes Of Light Reflected From A Surface Based On A Ring-Resonator," and filed on Aug. 3, 2005, both by inventors Frank Vollmer and Peer Fischer.

The above cross-referenced related applications are hereby incorporated by reference herein in their entirety.

STATEMENT REGARDING FEDERALLY SPONSORED RESEARCH OR DEVELOPMENT

Not applicable.

BACKGROUND OF THE INVENTION

1. Field of the Invention

The present invention relates to methods and devices for measuring optical properties such as refractive index, birefringence, and optical activity and for measuring and monitoring distances and changes thereof such as in interferometers and devices that can be used to profile surfaces such as scanning (near field) optical microscopes.

2. Brief Description of the Related Art

Many devices make use of various optical properties. For example, a camera makes use of the fact that light can be refracted, reflected and focused. Other common optical devices include microscopes and telescopes. Optical properties such as refractive indices have many other useful applications, including use in measuring a thickness of a thin film on a substrate.

The refractive index of a medium generally may be defined as the relative speed at which light moves through a material with respect to its speed in a vacuum. When light passes from a less dense medium (such as air) to a denser medium (such as water), the speed of the light wave decreases. Alternatively, when light passes from a denser medium (such as water) to a less dense medium (such as air), the speed of the wave increases. By convention, the refractive index of a vacuum is defined as having a value of 1.0. Since a vacuum is devoid of any material, refractive indices of all transparent materials are therefore greater than 1.0.

The angle of refracted light is dependant upon both the angle of incidence and the composition of the material into which it is entering. The "normal" is defined as a line perpendicular to the boundary between two substances. Light will pass into the boundary at an angle to the normal and will be refracted according to Snell's law:

$$N_1 \sin(\theta_1) = N_2 \sin(\theta_2)$$

where $N_1$ and $N_2$ represent the refractive indices of material 1 and material 2, respectively, and where $\theta_1$ and $\theta_2$ are the angles of the light traveling through materials 1 and 2 with respect to the normal.

Many methods and devices for measuring a refractive index of a medium are known. One such common device is known as a refractometer. A refractometer uses what is referred to as the "critical angle" of total reflection to measure the refractive index. When light passes through a medium of high refractive index into a medium of lower refractive index, the incident angle of the light waves becomes an important factor. If the incident angle increases past a specific value (dependant upon the refractive indices of the two media), it will reach a point where the angle is so large that no light is refracted into the medium with lower refractive index. This specific value is the "critical angle." The critical angle may be measured by transmission (light is transmitted through a sample) or by internal reflection (light is reflected from the boundary between the sample and the prism) when a sample is placed adjacent a prism.

Other methods or devices such as those disclosed in U.S. Pat. No. 6,490,039 and U.S. Patent Application Publication Nos. US2003/0098971, US2002/0140946 and 20040023396 likewise are known.

Birefringence occurs when an optical material in the path of a beam of light causes the beam to be split into two polarization components which travel at different velocities. Birefringence is measured as the difference of indices of refraction of the components within the material. Birefringence is an intrinsic property of many optical materials such as crystals but may be introduced by external fields applied to the material. The induced birefringence may be temporary, as when the material is strained, or the birefringence may be residual, as may happen when, for example, the material undergoes thermal stress during production of the material. The residual birefringence in an optical component affects its quality, especially when used in polarization related instruments. Linear birefringence refers to a difference in the refractive indices of two orthogonal linearly polarized light beams. Similarly, circular birefringence describes a difference in the refractive indices that right- and left-circularly polarized light experiences as it traverses the sample exhibiting circular birefringence. Birefringence (both linear and circular) may be observed as the rotation of the plane of polarization of a linearly polarized light beam.

A ring resonator can be built from standard fiber optics components, in the simplest form using only a fiber optic loop and a standard telecommunications coupler. One input of the coupler is connected to its output port closing the fiber loop. The remaining two ports form the connectors for a linear bus waveguide (fiber) which is used to couple the light evanescently into the ring structure.

Micro- and nanofabrication techniques make it possible to fabricate waveguiding structures out of a variety of materials and on a multitude of substrates. Ring resonators have been constructed with waveguides made from materials such as silica, silicon, and polymers (PMMA). Soft lithographic and micro-contact printing techniques can also be employed to manufacture waveguides.

The transmission characteristic of a ring resonator strongly depends on the frequency of the light—at specific frequencies the resonance condition for constructive/destructive interference is met when the light couples between the bus waveguide and the ring structure. The associated resonance frequencies can be determined with highest precision since the linewidth of the laser and the associated linewidth of the ring resonator is typically low. We routinely achieve resonances in a fiber-loop resonator that have sub-picometer linewidths.

The nature of the fiber or waveguide in general also accommodates modes with different polarization states. Each resonance is associated with a certain state of polarization (SOP), i.e. for instance (transverse electric) TE or (transverse magnetic) TM, and birefringence in the fiber-loop means that the different polarization states can have different resonance frequencies. The resonance frequencies can be measured by e.g. mode-hop free scanning of a tunable laser.

Ring resonators and related topics have been discussed in the following references: [1] U.S. Pat. No. 6,842,548 Loock, et al. Jan. 11, 2005; [2] A.V. Kabashin, P. I. Nikitin, Quantum Electronics 27 (1997) 653-654; [3] V.E. Kochergin, A. A. Beloglazov, M. V. Valeiko, P. I. Nikitin, Quantum Electronics 28 (1998) 444-448; [4] L. F. Stokes, M. Chodorow, H. J. Stokes, Opt. Lett. 7 (1982) 288-290; [5] F. Zhang, J. W. Y. Lit, J. Opt. Soc. Am. A. 5 (1988) 1347-1355; [6] J. E. Heebner, V. Wong, A. Schweinsberg, R. W. Boyd, D. J. Jackson, IEEE J. Quant. Elec 40 (2004) 726-730; [7] C-Y. Chao, L. J. Guo, Appl. Phys. Lett. 83 (2003) 1527-1529; [8] M. Brierley, P. Urqhart, Appl. Opt. 26 (1987) 4841-4845; [9] S. J. Petuchowski, T. G. Giallorenzi, S. K. Sheem, IEEE J. Quant. Elec. QE-17 (1981) 2168-2170; [10] L. H. Jae, M. Oh, Y. Kim, Opt. Lett. 15 (1990) 198-200; [11] D. Monzon-Hernandez, J. Villatoro, D. Talayera, D. Luna-Moreno, Appl. Optics 43 (2004) 1216-1220; and [12] A, Gonzalez-Cano et. al, Appl. Optics 44 (2005) 519-526. [13] U.S. Pat. No. 6,901,101 Frick May 31, 2005; [14] F. Vollmer, P. Fischer, Opt. Lett. 31 (2006) 453.

Various methods and apparatus for measuring optical properties, distances, etc. exist, but a need is present for the method and apparatus of the present invention, which measure optical properties with great sensitivity (via changes in the resonance frequency) and which lends itself to miniaturization as it requires no moving parts or electro-optic elements.

SUMMARY OF THE INVENTION

The present invention makes use of an optical ring-resonator in the form of a fiber-loop resonator, or a race-track resonator, or any waveguide-ring or other structure with a closed optical path that constitutes a resonator or cavity. The cavity is coupled to a tunable laser source such that the resonance wavelength can be determined from the transmission characteristics of the ring resonator. Introduction of a sample or a change in the length of the optical path gives rise to absolute shifts of the resonance frequencies and/or other changes of the characteristics of the transmission spectrum. The system is characterized by i) resonances in the ring or equivalent structure and ii) resonances that may be observed as spectral features (e.g. reduced or enhanced intensities) at a detector as the wavelength of the laser source is scanned. The sample is introduced into the resonant ring and relative and/or absolute shifts of the resonance frequencies are observed or other changes in the spectral features. The shift of the resonance frequency is a function of the refractive index of the sample. In the case of birefringence measurements, rings that have modes with two (quasi)-orthogonal polarization states are used, and the relative shifts of the resonance frequencies of these modes are observed. The present invention further comprises a method and apparatus for measuring and monitoring distances and physical properties based on a variable size ring-resonator.

Embodiments of the present invention concern fiber-loop ring resonators, racetrack ring-resonators and any other waveguide realizations of traveling-wave Fabry-Perot resonators and resonant ring sensors. The resonator may be formed by several different optical fibers or waveguides. The invention requires that the optical path of the resonator includes a gap, i.e. one or more segments where there is no waveguide or where the waveguide is replaced by a different medium. That medium may also be a waveguide with different material properties, but most likely it is simply free space, i.e. air. The gap may contain any number of additional optical, electrical, mechanical elements, flow cells, etc. After the gap there may be a reflecting surface, such as a mirror. The resonator that contains gap(s) (and possibly mirror(s)) is of such a nature that it still allows (at least for some time) the light to form a closed optical path such that the resonator exhibits transmission characteristics associated with resonant cavities of its class. The resonator that incorporates a gap may in particular sustain resonant modes that are characterized by different properties, such as different states of polarization. The size of the gap (and thereby the size of the ring resonator) may change with pressure, temperature, vibrations, strain, etc. and the device can thus be used to monitor and measure these properties and/or any other physical, chemical or biological property that can alter the gap dimension.

In another embodiment of the invention the ring-resonator contains a reflecting surface in its optical path and the gap between the waveguide and the reflecting surface is measured. The invention can thus be used for laterally raster-scanning the surface (in the directions perpendicular) to the wave-guide. The device may in particular be used to study the surface relief of thin-films, coatings, biological material, and any other sample that is reflective or made to be reflective (e.g. through an appropriate metal coating, or reflection from a suitable dielectric). Similarly opaque samples placed on a reflective surface may be studied by monitoring a change in one or more performance characteristics of the resonator, such as changes in the linewidth of the resonances, as the sample is scanned laterally.

In still another embodiment of the invention the ring-resonator contains a reflecting surface in its optical path, and the gap distance is not changed, but the light is incident on the surface structure such that a surface plasmon resonance is excited by the light. For certain angles of incidence the surface-plasmon resonance (SPR) causes the reflectance to be at a minimum and simultaneously the phase of the p-polarized light undergoes a phase change different from the s-polarized light. It is known that the phase change of p-polarized (relative to s polarized) light as a function of the angle of incidence of the light can be a particularly sensitive means of observing SPR. The modes associated with the two polarization states (s and p polarized light) will have different resonance frequencies in the ring resonator and/or other performance characteristics. Monitoring the (relative) resonance frequencies and/or other performance characteristics and their possible change allows for frequency domain phase measurements of the surface plasmon resonance phenomenon and for a sensitive embodiment of a surface plasmon resonance sensor. Such a sensor can be used to detect biomolecules, bacteria viruses etc. binding to the metal surface since this binding is associated with a phase change of the SPR. In addition laterally scanning the surface makes is possible to obtain images of surfaces, possibly biological micro-array sensors, as a function of the relative change in resonance frequency between the modes that give rise to s and p polarized light. The embodiment has all the capabilities a standard surface plasmon resonance sensor has, but in addition it is able to measure and monitor the phase of the reflected light associated with the SPR phenomenon in real time and conveniently through relative frequency measurements.

Other embodiments of the present invention build on the previously proposed gap and the method to measure (polarization dependent) optical properties in a ring resonator and related resonators. The principle of operation rests on the fact that the resonance frequency and other performance characteristics change with the size of the ring (optical path length in the resonant cavity), and therefore are a direct function of the gap dimension, or spacing between the waveguide and a reflecting surface. The invention can be used to:

- monitor the gap dimension, i.e. separation between waveguides or separation between a waveguide and a reflecting surface
- obtain the surface relief of a reflecting or partially reflecting surface
- construct a novel surface reflectance scanning microscope
- build a sensor that is sensitive to changes in the gap dimension which in turn can be used to monitor distance, displacement, vibration, pressure, strain, temperature, etc.

In addition, the invention also details how any phase changes that arise from the reflectance of a surface can be measured. For instance, it is known that p-polarized light can excite a surface plasmon resonance in a thin metallic film if the light is incident from a suitable dielectric at a specific angle of incidence. Conventionally a change in reflectance (minimum) near the surface plasmon resonance angle is measured. In addition the concomitant phase change that p-polarized light experiences may be measured in a resonator. In particular, if two modes are present, then the modes that give rise to p-polarized light will have changes in their performance characteristics different from those modes that give rise to s-polarized light. Measuring and monitoring the relative changes in the performance characteristics of these modes allows the surface plasmon (or for that matter any other, possibly polarization dependent, phase change upon reflection) to be monitored and measured. A scanning surface microscopy that incorporates the measurement of the phase upon reflection using a resonator can thus be realized.

In a preferred embodiment, an optical device of the present invention comprises an optical resonator having an optical path, means for tuning a frequency of a narrow linewidth coherent light source, means for coupling light from the light source into the resonator, a monitoring system that detects at least one performance parameter of the resonator such as the resonance frequencies of the resonator, and a signal processor coupled to the monitoring system to process the output, wherein the signal processor comprises an optical detector. The optical resonator may comprise at least one of a fiber-loop resonator, a circular waveguide, a racetrack resonator, a disk resonator, a toroidal resonator, a spherical resonator, and a photonic crystal resonator. The narrow linewidth coherent light source comprises a laser.

The optical resonator in a preferred embodiment of the present invention may be fabricated from at least one of silica, silicon or a polymeric material and may have at least one gap. The optical resonator confines an electromagnetic wave which leaves a waveguide of the optical resonator and enters a different medium before re-entering the waveguide of the ring-resonator. The different medium may comprise, as an example, air. The gap may be a separation between two cleaved, aligned fiber ends, may be one or more etched segments in a fabricated waveguide, or may be a hole in a waveguide. Further, the gap may comprise porous silicon.

The optical resonator may comprise at least one reflecting surface which may comprise at least one selected from the group of a metallic, a dielectric and a multilayer structure. The reflecting surface also may comprise a mirror or may be directly deposited on at least a portion of the optical resonator. The reflecting surface may be located in the gap of the ring resonator. The reflecting surface further may be a sample coated with a metal. The reflecting surface further may comprises a metal surface, such as gold or silver for example, that has been functionalized with suitable surface preparation and/or chemistry to be used as a biological, chemical sensor. The metal surface may comprise antibodies or oligonucleotides surface immobilized on a metal film. The reflecting surface may be only partially reflecting, non-uniform and/or optically flat. The reflecting surface may be located at an end of a linear waveguide(s).

In various embodiments of the invention, the optical device may further comprise at least one of a fiber port, a circulator, a laser, a polarizer, a waveplate, an objective lens, a lens system, a collimator for directing light, a prism, a beamsplitter, a tapered fiber, a metal coated fiber, an eroded fiber, an optical isolator, a directional coupler, a non-directional coupler, a computer, an optical detector, rotation stages, motorized stages, an optical table, vibration isolation, a flow cell, a pump, a microfluidic device, and a filter. In still other embodiments, the optical device of the present invention may further comprise means for handling at least one of liquids or gases, means for delivering a liquid sample wherein said means allows a sample to flow across a surface.

The detector may comprise at least one of a photodiode and a photomultiplier and a charged coupled detector and/or may comprise means for detecting a change in one or more characteristics of said optical resonator. The narrow linewidth coherent light source may comprise a laser and electronics for control of said laser. The electronics may comprise at least one of detection electronics such as lock-ins, function generators, data-acquisition boards, analog to digital converters, amplifiers.

The optical device of the present invention further may comprise a mechanical stage having a piezo-driver. Still further, the optical device of the present invention also may comprise at least one of a colored glass filter and a bandpass filter and neutral density filters.

A sample may be introduced in the gap, for example, between the reflecting surface and the waveguide. The sample may comprise, for example at least one of the following: a liquid, a solid, a gas, a crystal, a thin film, a metallic surface, a dielectric surface, tissue, biological samples viral particles, a polymer and a gel. A length of said gap may change and/or a distance between said waveguide and said reflecting surface may change. The distance or length of the gap may change due to temperature, or pressure, or strain, or vibration, or swelling of a polymer.

In still other embodiments, the reflecting surface in an optical device according to the present invention may be raster-scanned in the plane normal to the waveguide such that the surface relief of the reflecting surface or its thickness, or the optical properties of a sample introduced between the surface and the waveguide may be determined.

An optical device according to the present invention further may comprise several tunable, narrow linewidth coherent light sources multiplexed to said optical resonator. In still other embodiments, an optical device of the present invention comprises a plurality of optical resonators each having a different optical pathlength, a narrow linewidth coherent light source, wherein the plurality of optical resonators are multiplexed to the light source, a monitoring system that detects at least one performance parameter of the resonator such as the resonance frequencies of the resonator, and a signal processor coupled to the monitoring system (optical detector) to process an output of the monitoring system. The coherent source may comprise, for example, at least one of a distributed feedback laser and an external cavity laser and may or may not operate in a visible spectrum and may operate in a region of an electromagnetic spectrum that permits the observation of resonances. The resonances may be associated with modes having different states of polarization, modes that are described by predominately linear polarization states, or modes that are described by predominately circular polarization states. An angle of incidence of the light onto said reflecting surface may be changed without changing the overall pathlength of the ring-resonator.

A method for measuring an optical characteristic in accordance with the present invention may comprise the steps of (i) measuring a first value of a property of an output optical signal from an optical resonator in absence of a sample; and/or at a given position of the sample; and/or for a certain angle of incidence; and/or at a given time; (ii) measuring a second value of the property of the output optical signal from the optical resonator when a sample is in the optical path; and/or at a different lateral position of the sample/surface; and/or a different angle of incidence; and/or at a later time; and (iii) extracting information of the sample/surface/system from a difference between the first and the second values. The property comprises any performance parameter, and may, for example, be a resonance frequency, transmission spectrum, linewidth.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRITION OF THE DRAWINGS

For a more complete understanding of the present invention and the advantages thereof, reference is now made to the following description and the accompanying drawings, in which:

FIGS. 1(a)-(c) are diagrams of an optical ring resonator arrangement in accordance with a preferred embodiment of the invention.

FIGS. 2(a) and (b) are diagrams of coupling arrangements for ring resonators in accordance with preferred embodiments of the invention.

FIG. 3(a) is a diagram of an optical sphere resonator used in a preferred embodiment of the invention.

FIG. 3(b) is a diagram of an optical disk resonator used in a preferred embodiment of the invention.

FIG. 3(c) is a diagram of a reflected beam resonator used in a preferred embodiment of the invention.

FIG. 3(d) is a diagram of a photonic crystal resonator used in a preferred embodiment of the invention.

FIG. 4(c) is a block diagram of an apparatus for tapping light from a ring resonator using a beam splitter in accordance with a preferred embodiment of the invention.

FIG. 8(a) is a block diagram of an apparatus for rotating a sample cell in accordance with a preferred embodiment of the invention.

FIG. 11(a) is a diagram depicting data of a transmission spectra recorded in accordance with a preferred embodiment of the invention. The graph shows the change of the resonance frequencies of left (LCP) and right (RCP) circularly polarized resonant frequencies after adding S-limonene in an R-limonene solution (50% v/v final). The data is recorded from a detector in the linear waveguide.

FIG. 11(b) is a diagram depicting data of a transmission spectra recorded in accordance with a preferred embodiment of the invention. The graph shows the change of the resonance frequencies of left (LCP) and right (RCP) circularly polarized resonant frequencies after adding S-limonene in an R-limonene solution (50% v/v final). The data is recorded from a detector which tapped light from the resonant waveguide 750.

Figure 12:
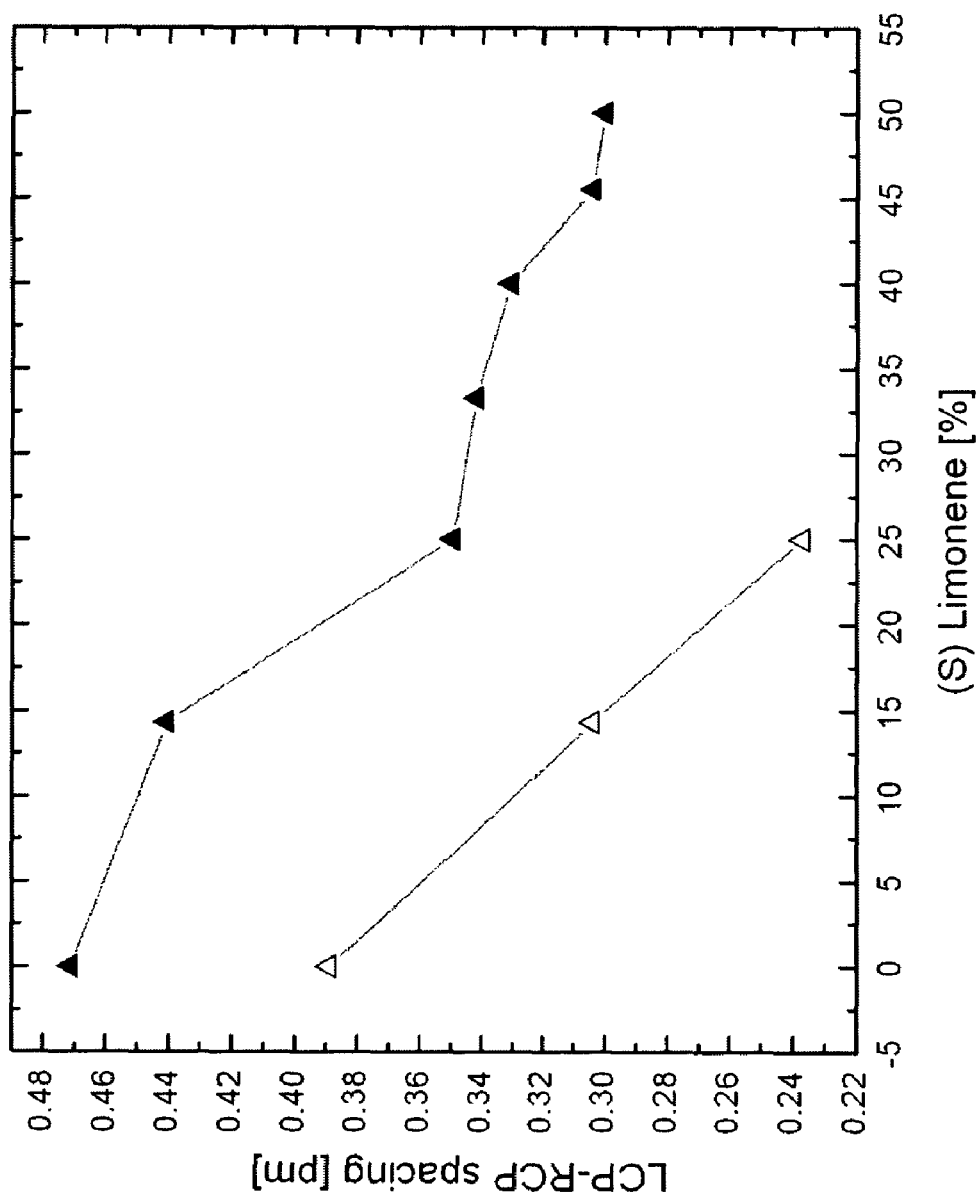

FIG. 12 shows that two independent measurements the slope of the curve are reproducible and are related to the change of refractive index with enantiomeric excess (volume of S-limonene titrated into a volume of R limonene).

Figure 13:
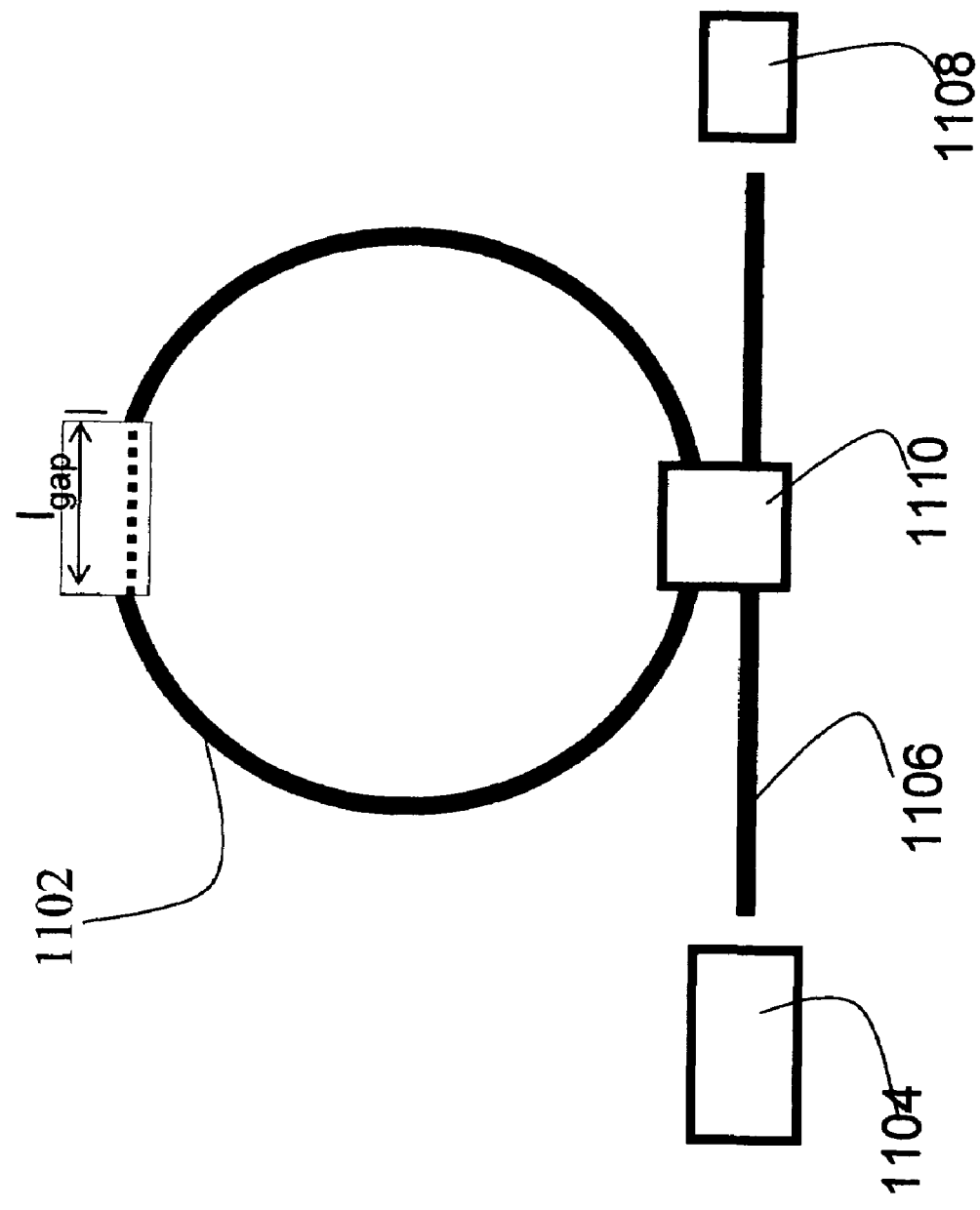

FIG. 13 is a resonant-ring structure in accordance with a preferred embodiment of the present invention.

FIG. 14 is a diagram of a preferred embodiment of the present invention in which a free-space beam traversing a gap located in-line with the resonant ring structure leaves and re-enters the waveguiding structure (here fiber) through a fiber-optic circulator and a fiber port.

FIG. 14a is a diagram of a reflecting surface with surface features.

Figure 15:
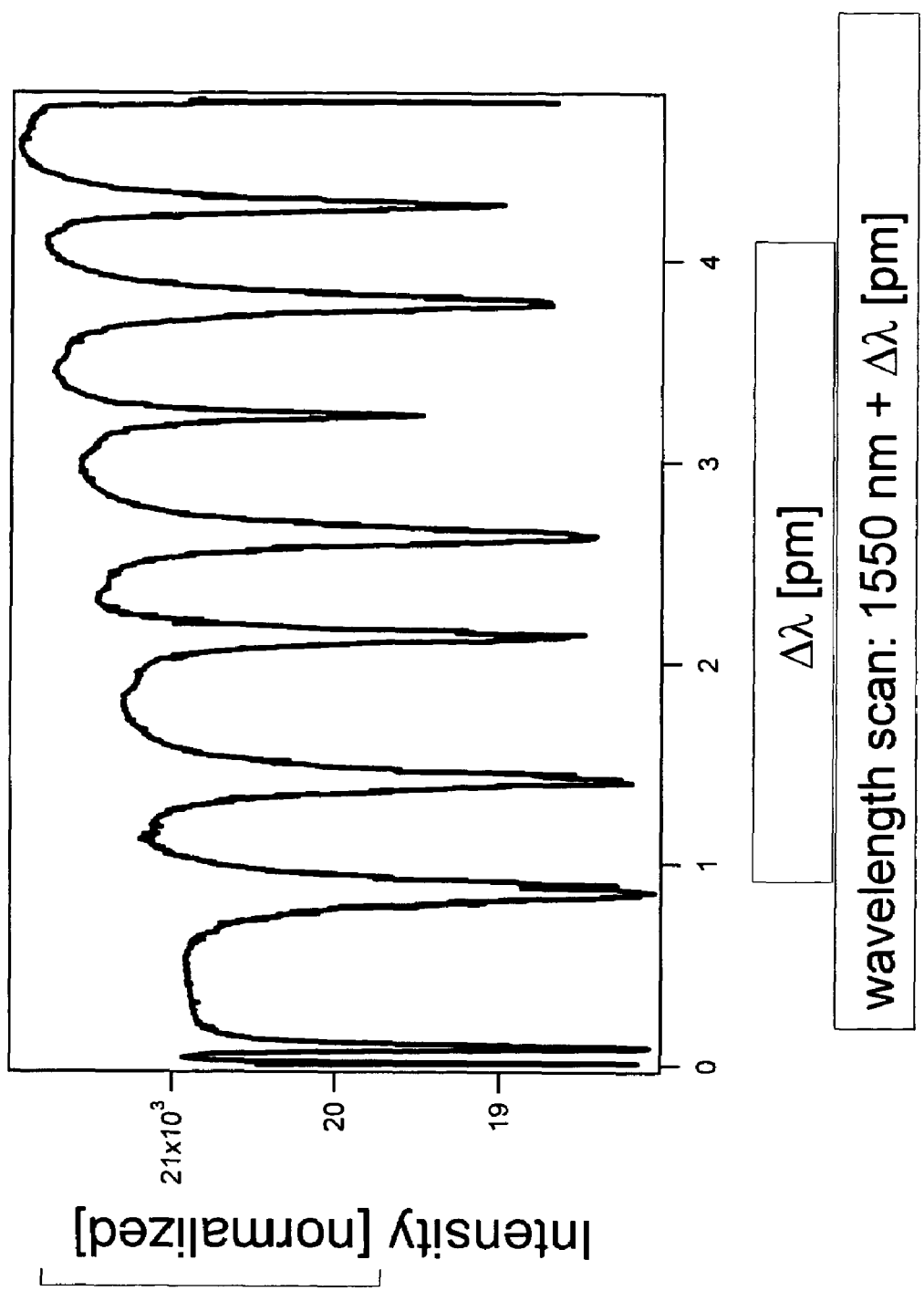

FIG. 15 is a graph of a spectrum obtained with setup shown in FIG. 14.

Figure 16:
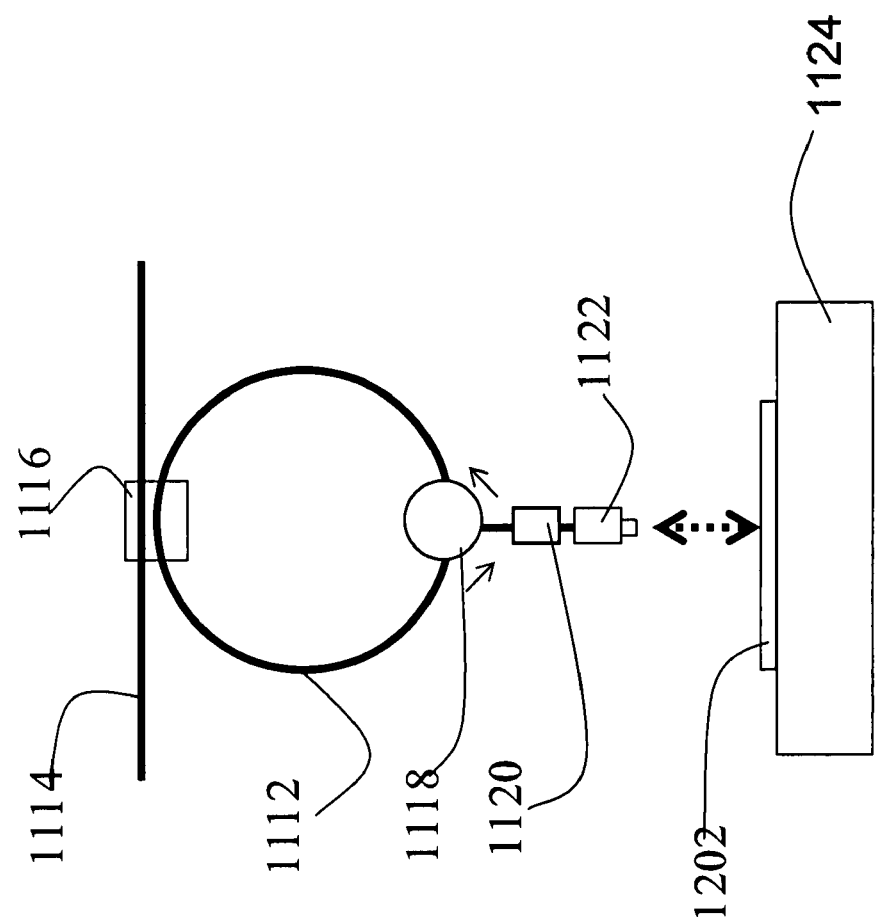

FIG. 16 is a diagram of a preferred embodiment of the present invention incorporated in a scanning microscope.

Figure 17:
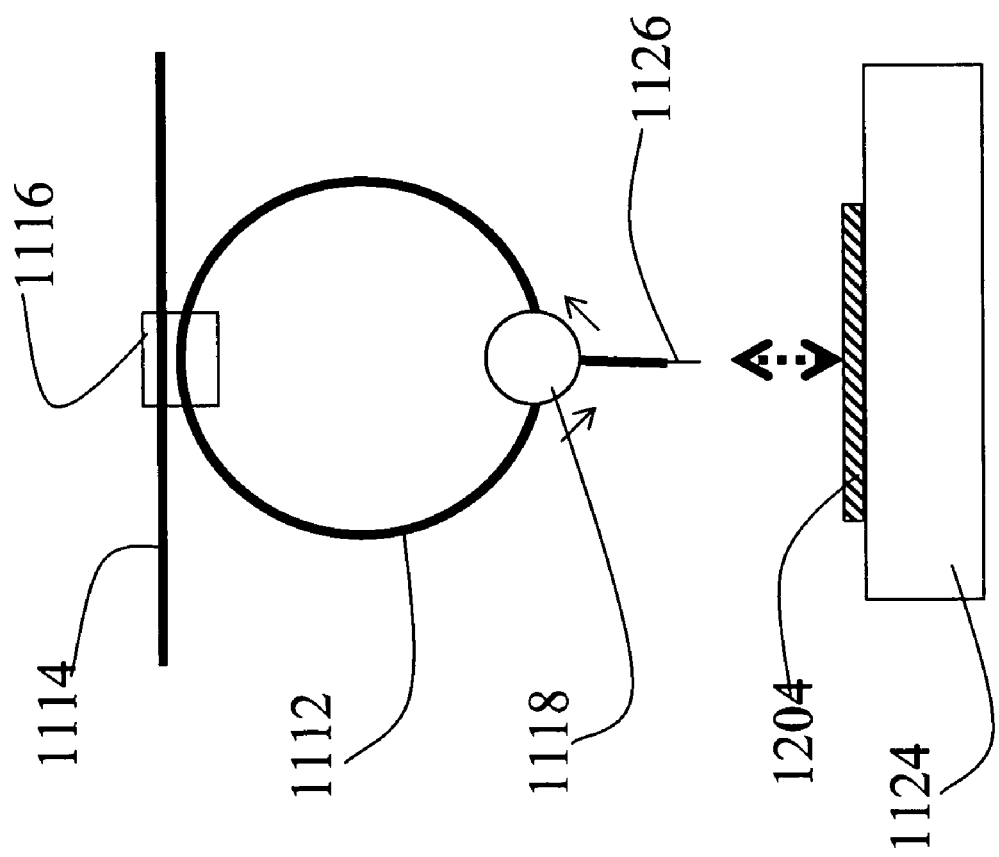

FIG. 17 is a diagram of a preferred embodiment o the present invention incorporated in a near field probe for a partially reflecting sample.

Figure 18:
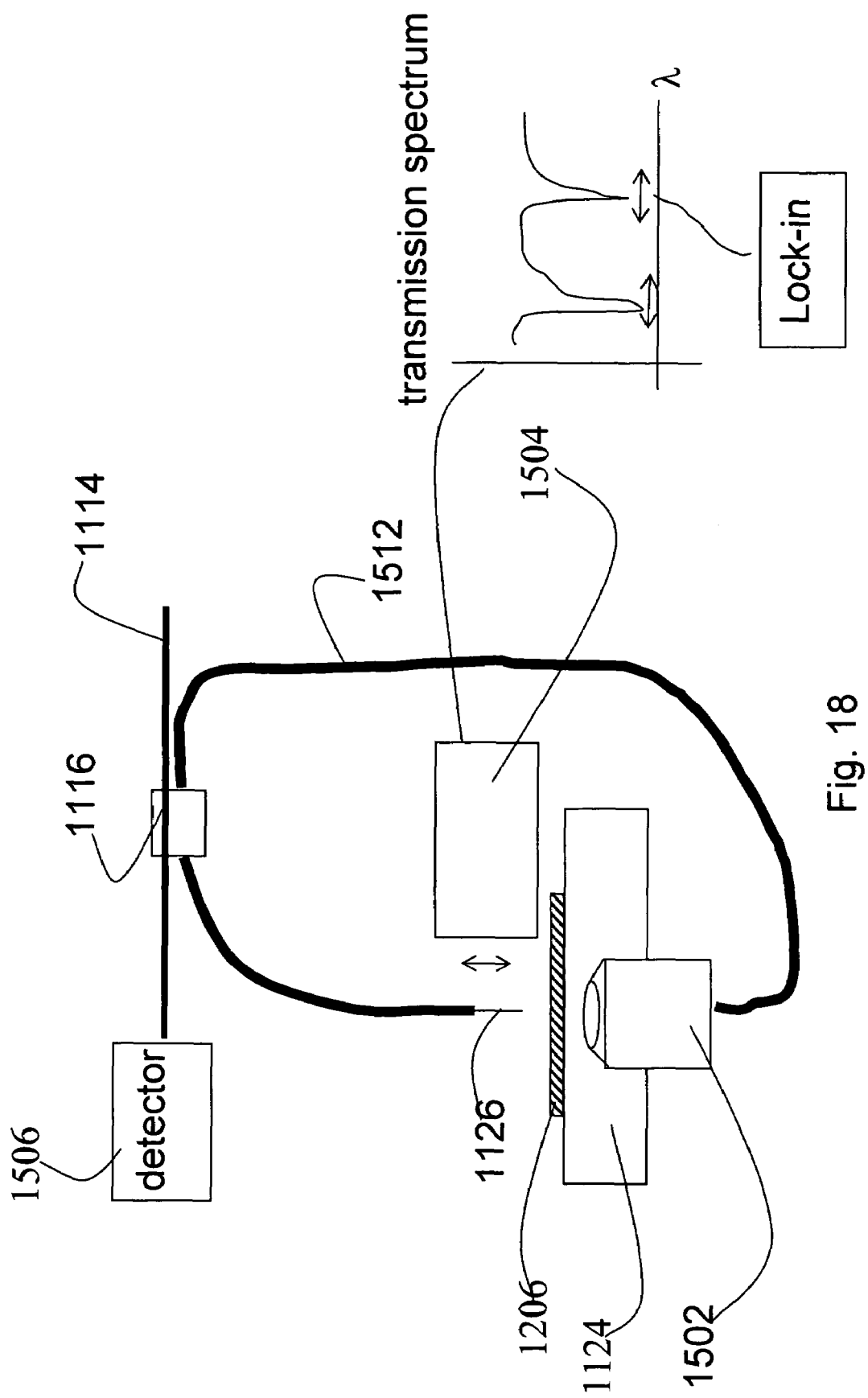

FIG. 18 is a diagram of a preferred embodiment of the present invention incorporated in a scanning microscope with an opaque sample similar to a near field optical microscope.

Figure 19:
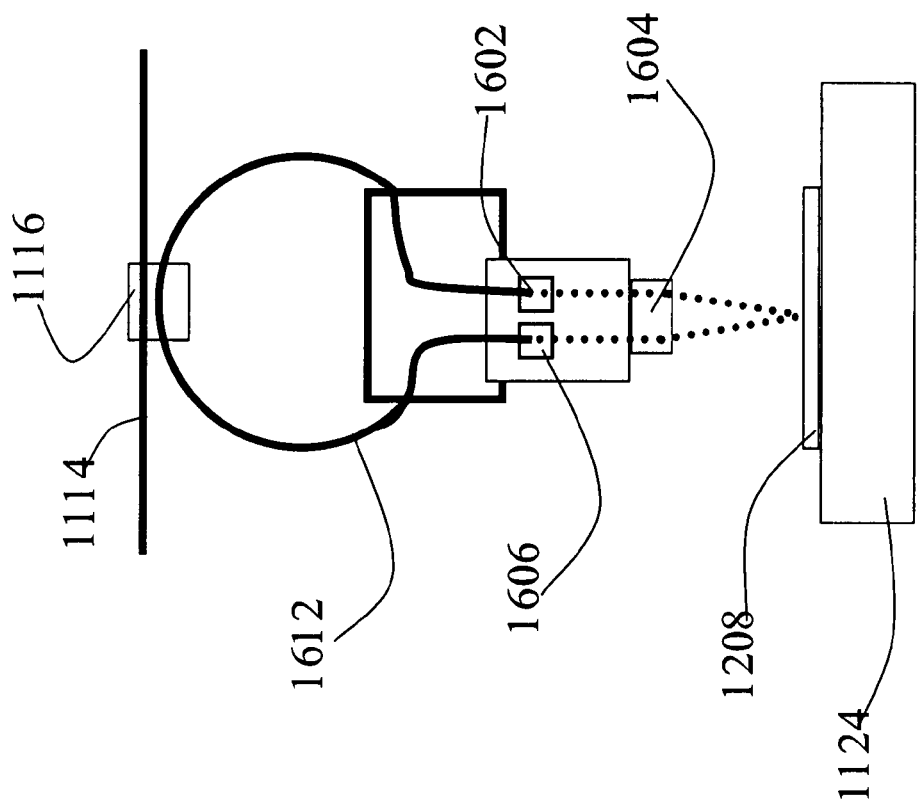

FIG. 19 is a diagram of a preferred embodiment of the present invention incorporated in a scanning microscope.

FIG. 20 is a diagram of a preferred embodiment of the present invention for information storage and retrieval.

FIGS. 21a and b are diagrams of a preferred embodiment of the present invention for distance measurements, pressure strain and vibration measurements.

Figure 22:
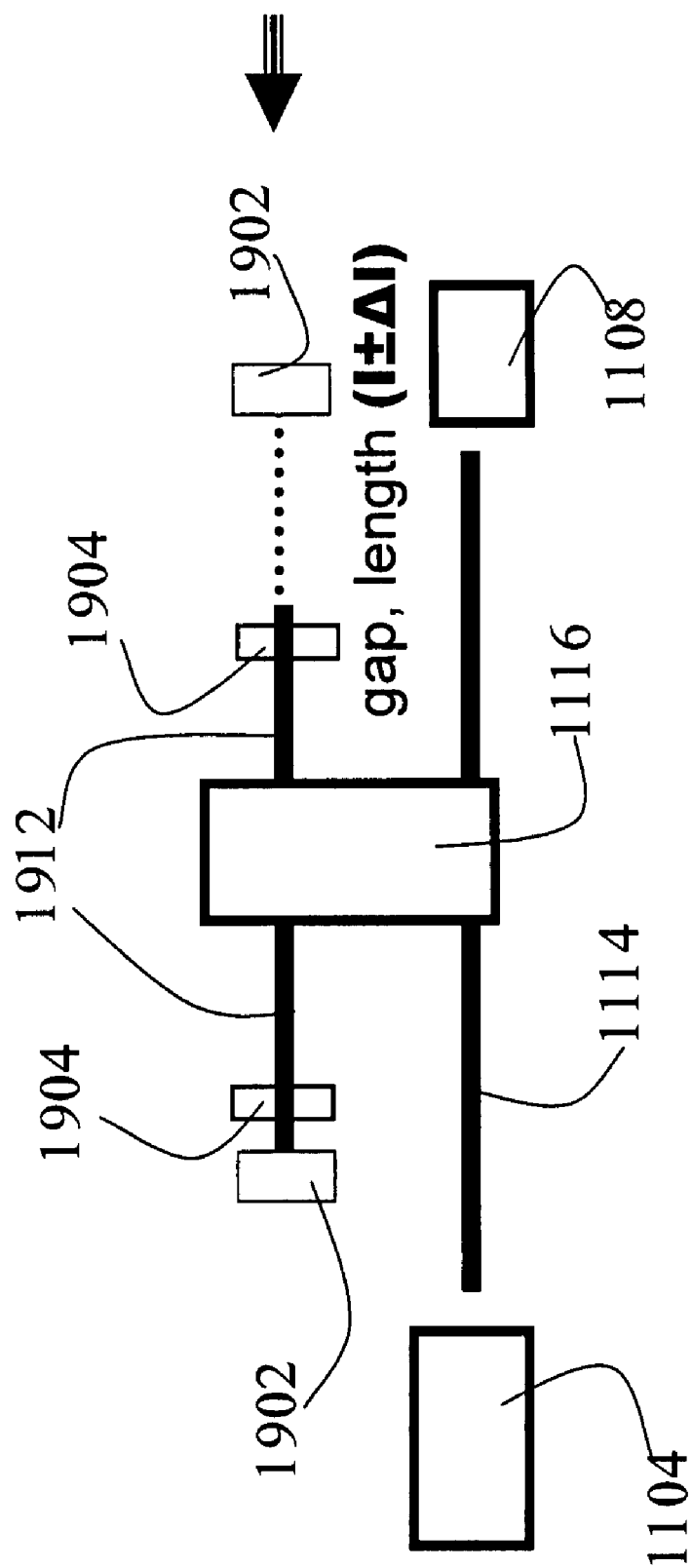

FIG. 22 is a diagram of a preferred embodiment of the present invention as a linear (one dimensional) cavity.

Figure 23:
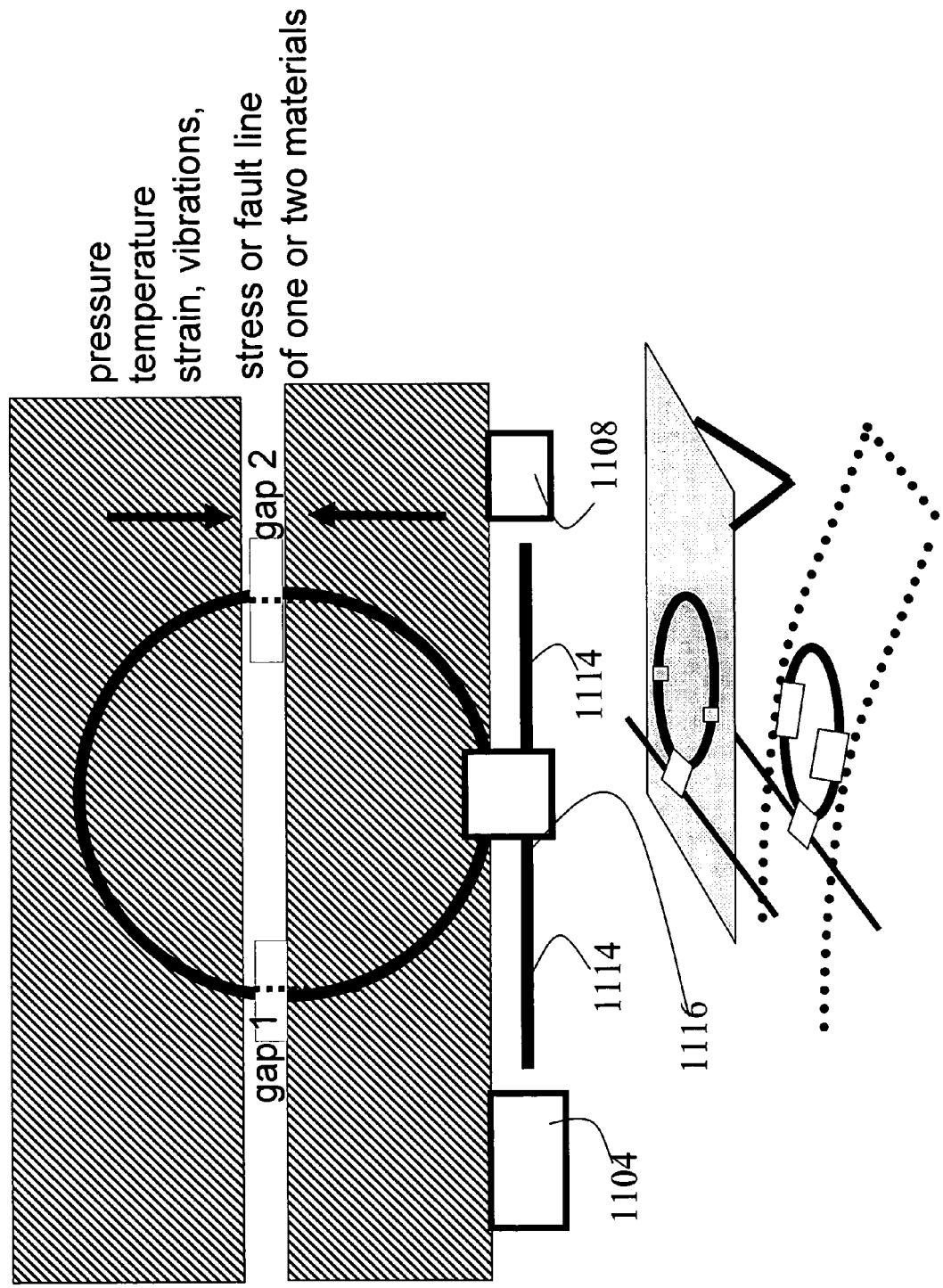

FIG. 23 is a diagram of a resonant ring with two inline gaps in accordance with a preferred embodiment of the present invention.

Figure 24:
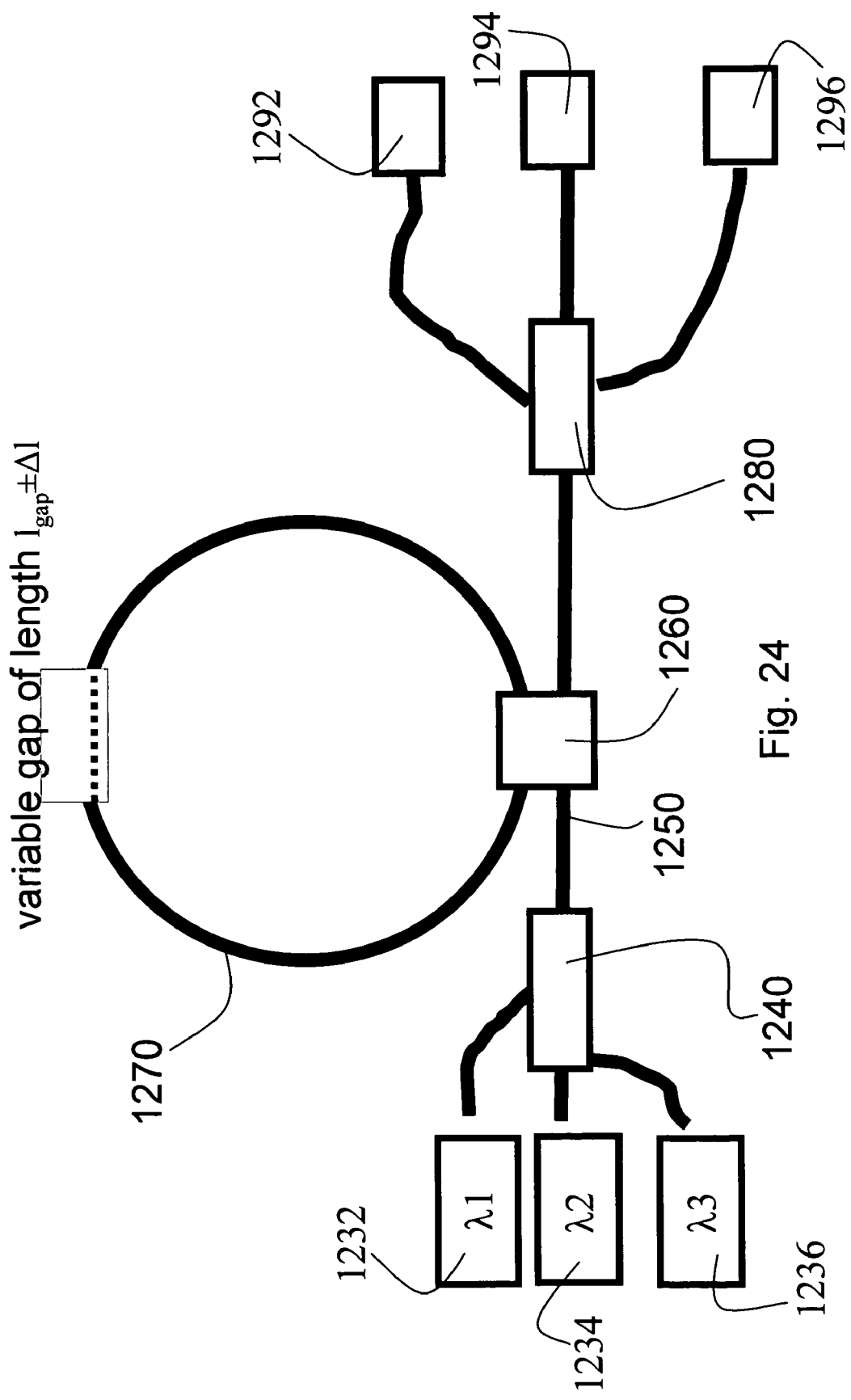

FIG. 24 is a diagram of a preferred embodiment of the present invention incorporating wavelength multiplexers and demultiplexers.

Figure 25:
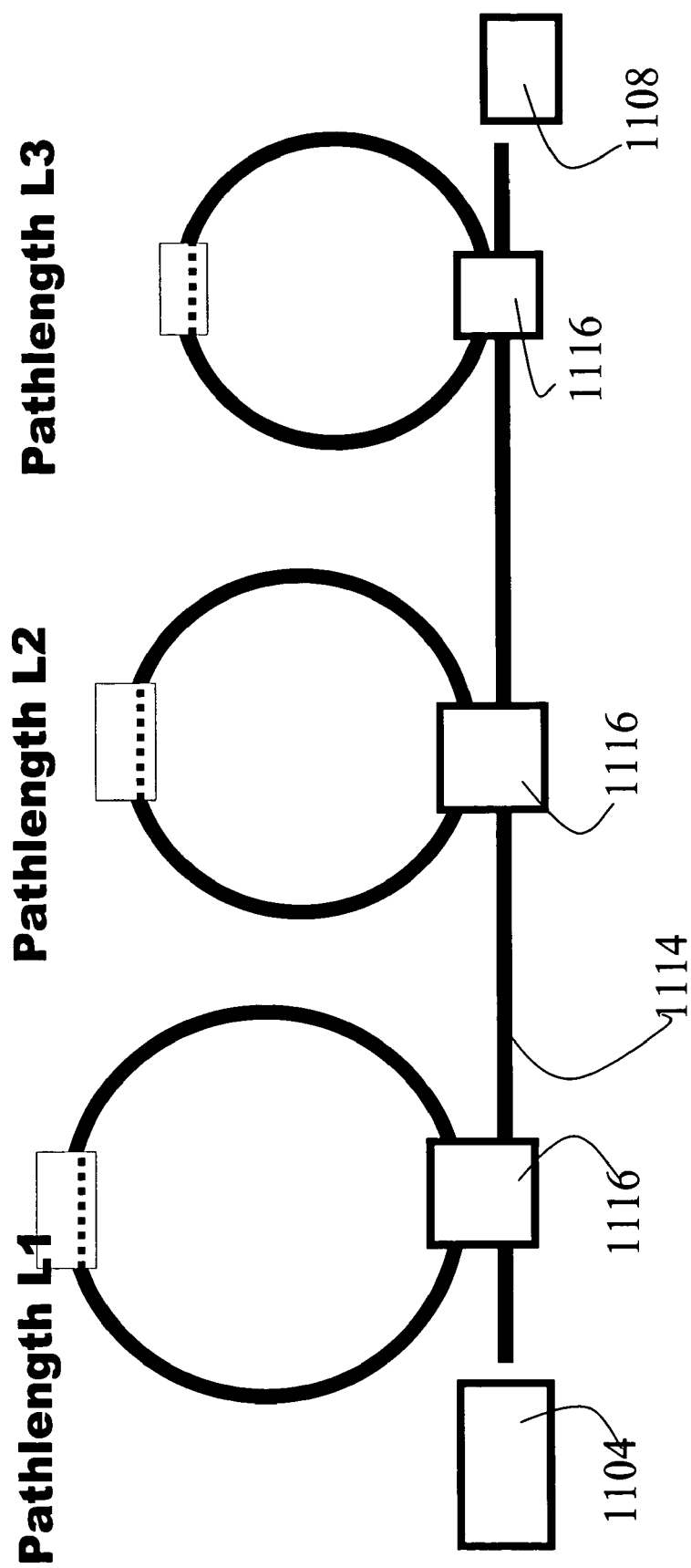

FIG. 25 is a diagram of a preferred embodiment of the present invention incorporating several multiplexed resonators of different pathlength L.

Figure 26:
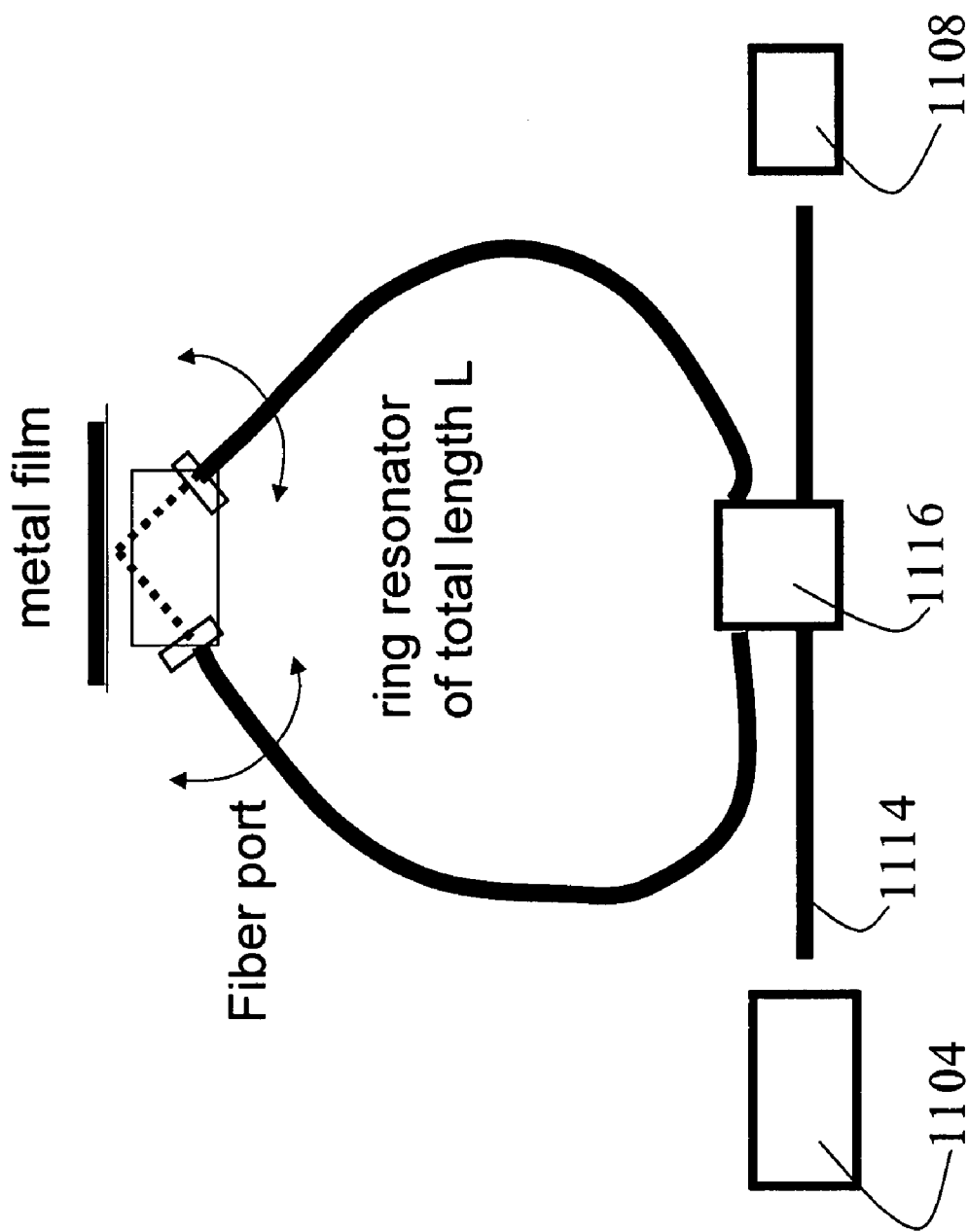

FIG. 26 is a diagram of a preferred embodiment of the present invention where the circular waveguide contains a reflecting surface or equivalent structure (dielectric multilayer) and is arranged such that the free space beam is incident onto reflecting surface at an angle.

Figure 27:
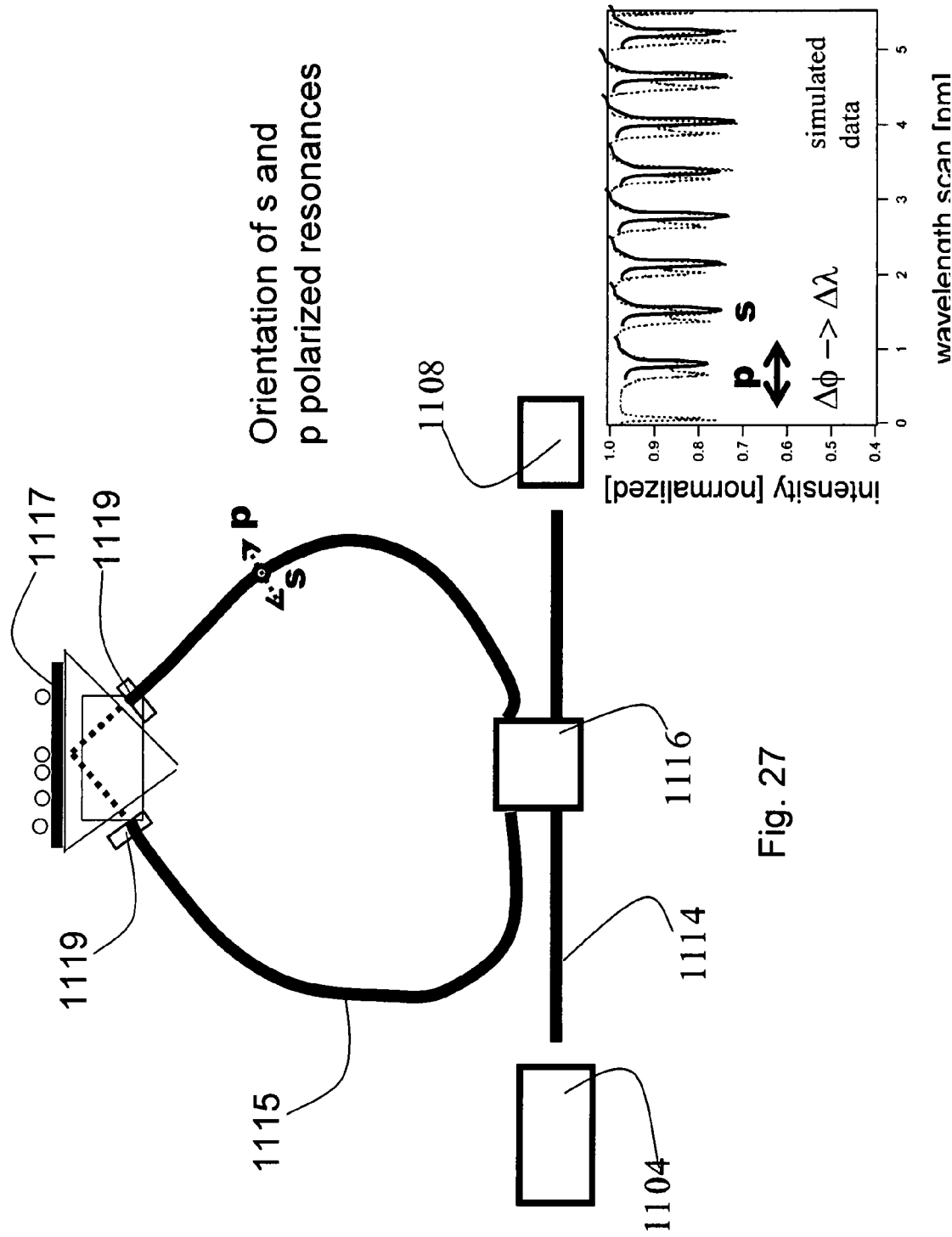

FIG. 27 is a diagram of a preferred embodiment of the present invention where the light is incident at an angle onto a metal surface via a prism or equivalent arrangement such that the light excites a surface plasmon resonance.

Figure 28:
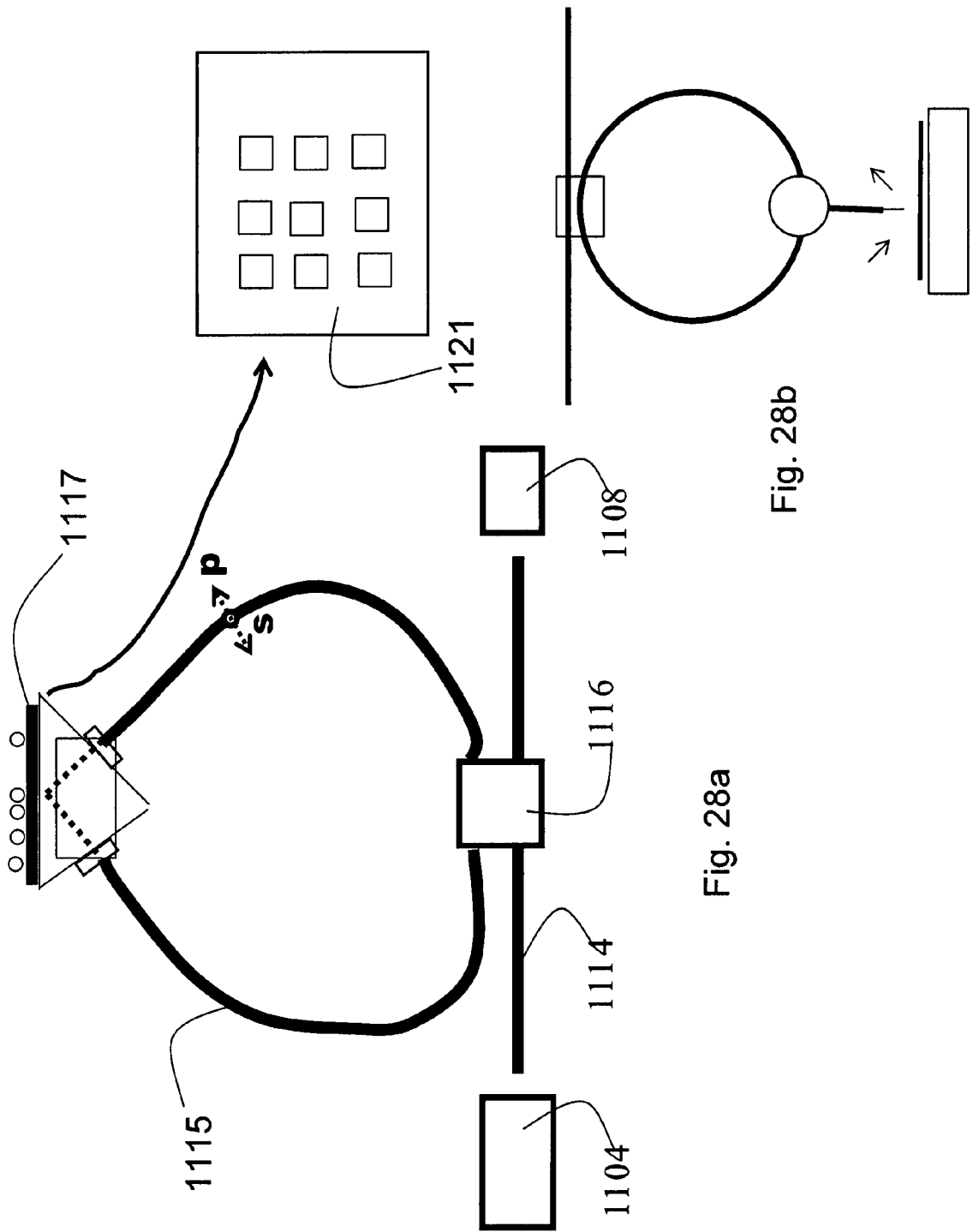

FIGS. 28a and b are diagrams of a preferred embodiment of the present invention as in FIG. 27 but with the addition that the surface may be raster-scanned to undertake "surface plasmon resonance phase-sensitive imaging" of surfaces.

Figure 29:
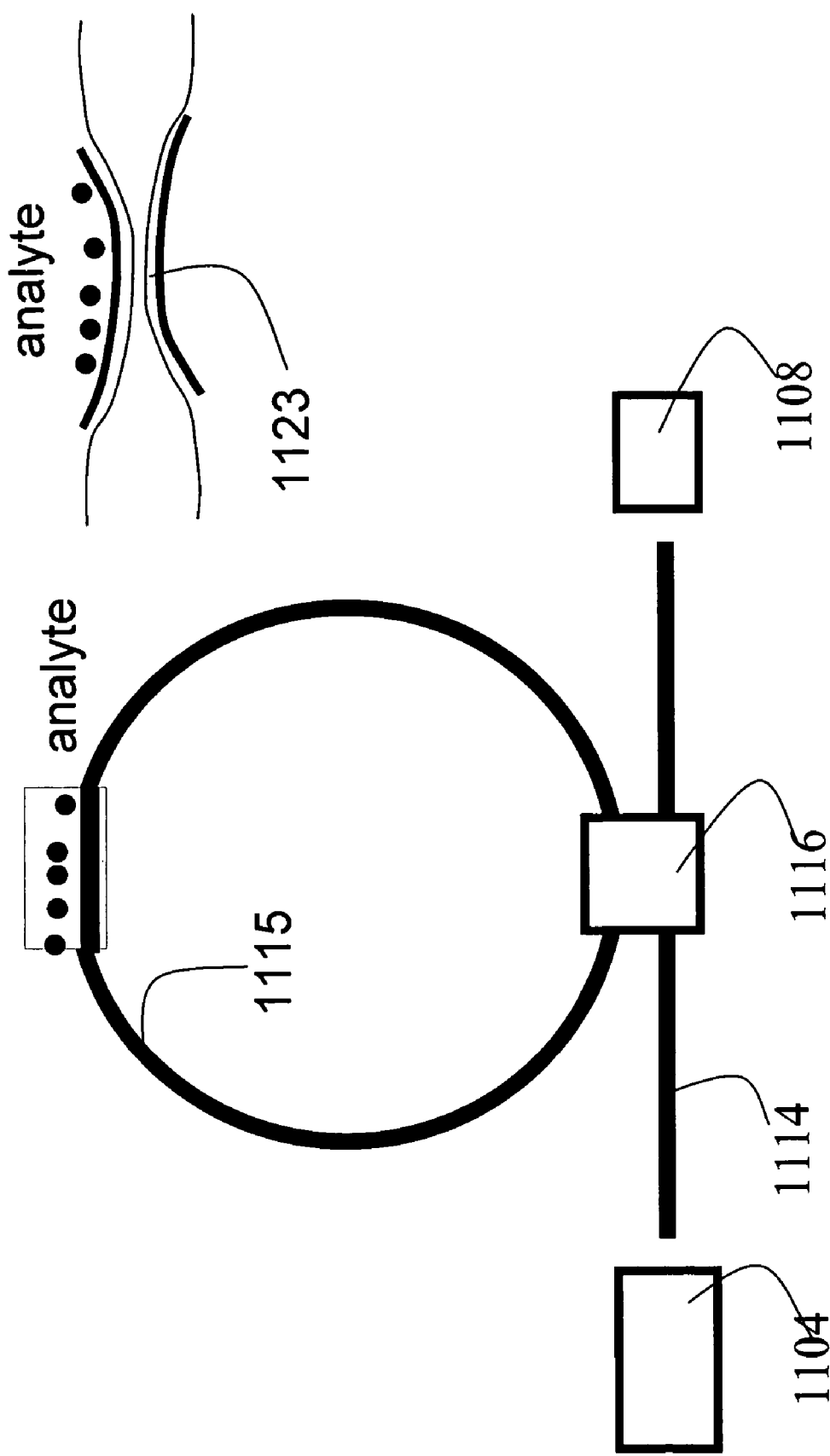

FIG. 29 is a diagram of a preferred embodiment of the present invention as an all-ring SPR coupled resonator.

Figure 30:
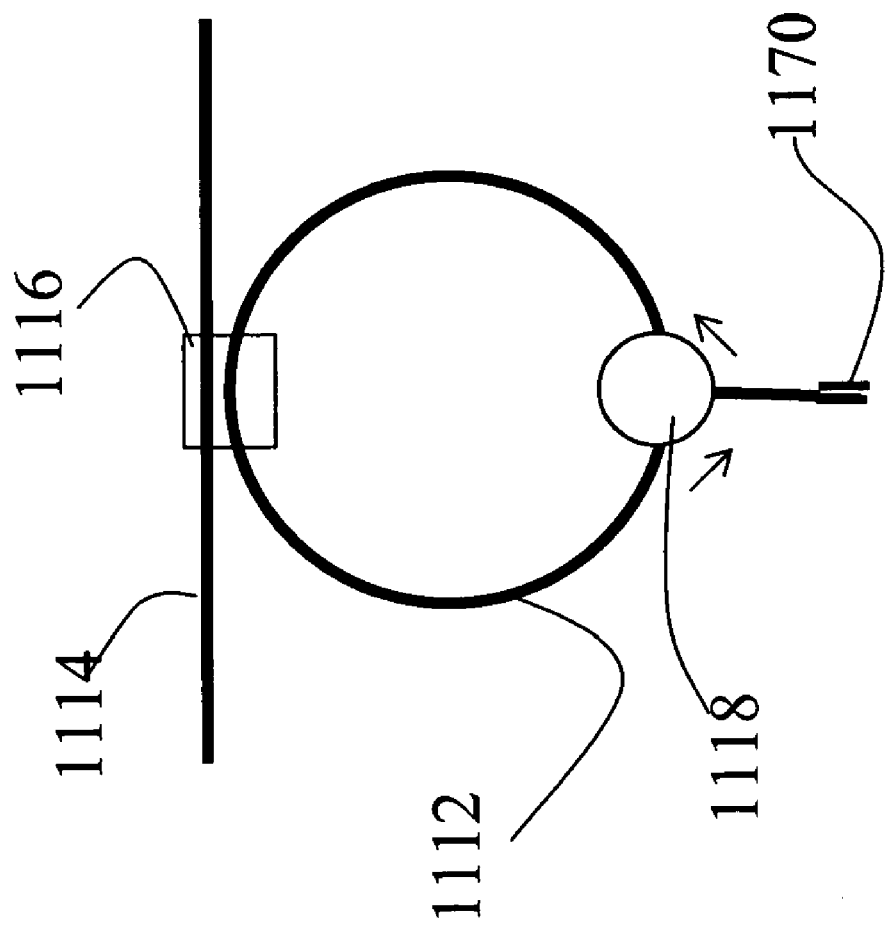

FIG. 30 is a diagram of a preferred embodiment of the present invention as FIG. 29 except that a fiber optic circulator is introduced in the fiber loop.

DETAILED DESCRIPTION OF THE PREFERRED EMBODIMENTS

In a preferred embodiment of the present invention, a sample cell 150 is introduced into an optical resonant structure, such as the ring-resonator 110 shown in FIG. 1(a). The term "ring-resonator" is used herein to refer to any structure with a closed optical path that constitutes a cavity, such as fiber-loops, race-track resonators, or other appropriate waveguiding structures.

The light may be propagated to and from the resonant structure using a waveguide referred to as a "linear" waveguide 120. The coupling arrangement 130 couples the linear waveguide 120 to the ring structure 110, e.g. through an evanescent field. There are different arrangements for the coupling region between linear waveguide 120 and ring resonator 110 as shown in FIGS. 2(a) and (b). The linear waveguide provides the connection to a laser source (not shown) and to a detector (not shown). For a linear waveguide, different waveguide profiles having a waveguide core 112 and a protective cladding 114 are possible (FIG. 1(c) and (d)). The resonant structure can be operated in air or it can be immersing in a liquid. While a ring-resonator is described in the preferred embodiments herein, optical resonant structures for use in the present invention may be built from linear waveguides, microspheres (FIG. 3(a)), disks (FIG. 3(b)), opposed mirrors (FIG. 3(c)), ring photonic crystals (FIG. 3(d)), laser cavities, micro or nanofabricated waveguides or equivalent structures. In each case the sample is introduced in the light path of the cavity. This can be achieved by engineering gaps or pores or other equivalent structures into the resonant cavities or by fabricating a porous or hollow (section of) the ring resonator. The waveguides may be made from, for example, silicon or silica, may be easily integrated with electronics, and may be miniaturized with micro-nanofabrication techniques such that an all-optical lab on a chip is possible. The waveguide structure may also be engineered to be asymmetric and may for instance include twists or be of a special shape such that the resonator is described by modes that have polarization states which facilitate the measurements proposed in this invention.

Such optical resonant structures may be used for spectroscopy with solids, thin films, liquids, and other transparent materials. This optical resonant spectroscopy allows for the determination of optical properties such as linear birefringence, circular birefringence, refractive index, enantiomeric excess, chirality, optical rotations, optical activity, etc., with high sensitivity. The resonant structure allows the apparatus to measure two orthogonal polarization states of the light at different frequencies. The orthogonal states can be quasi-TE/TM or left circular/right circular. It is possible to select either linearly or circularly polarized resonant light modes, either due to the intrinsic structure of the waveguide or by use of appropriate waveplates or equivalent optical components (including reflecting elements) inserted in the resonant structure and/or inserted into the linear part of the waveguide circuit.

Figure 4A:
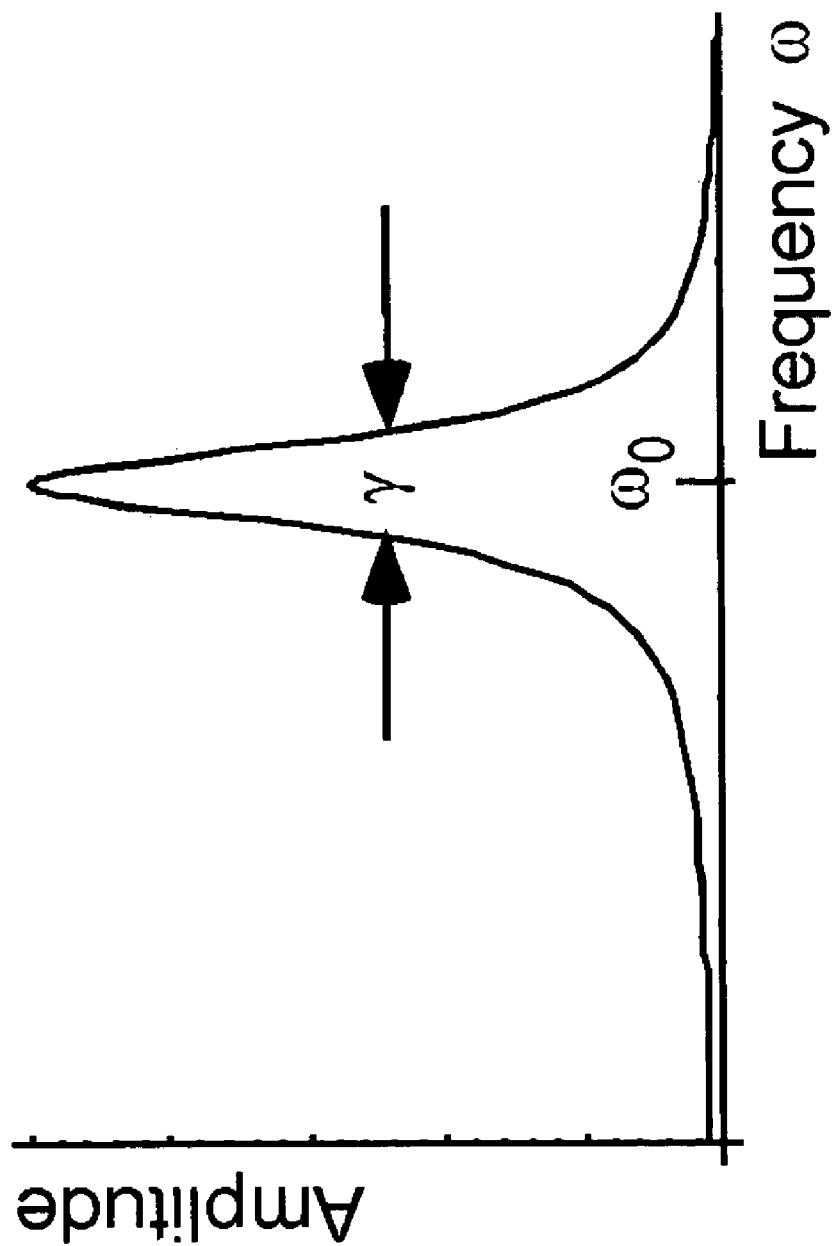
FIG. 4(a) is a graph showing the resonance frequency $\omega_0$ and the linewidth $\gamma$ (gamma).
Figure 4B:
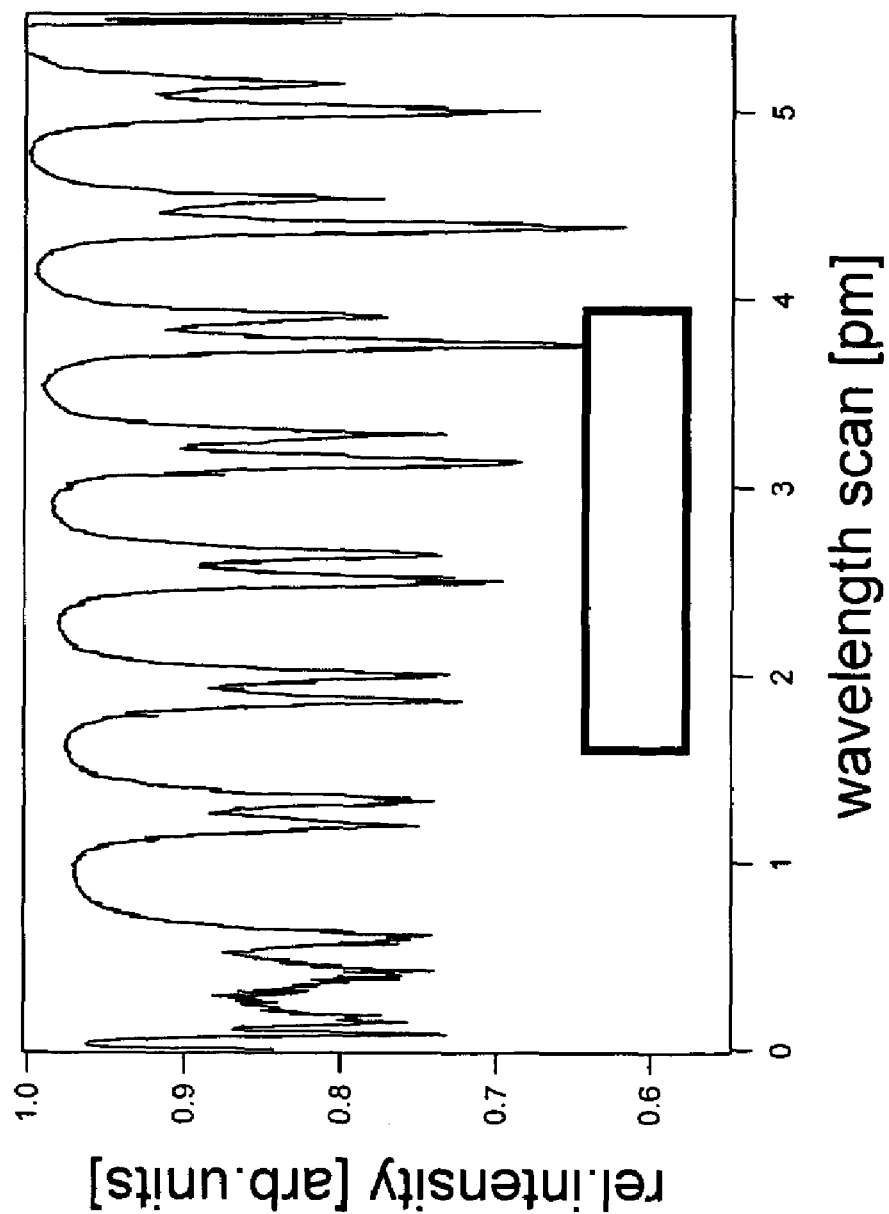
FIG. 4(b) is a graph illustrating resonances in a fiber ring.
Figure 5A:
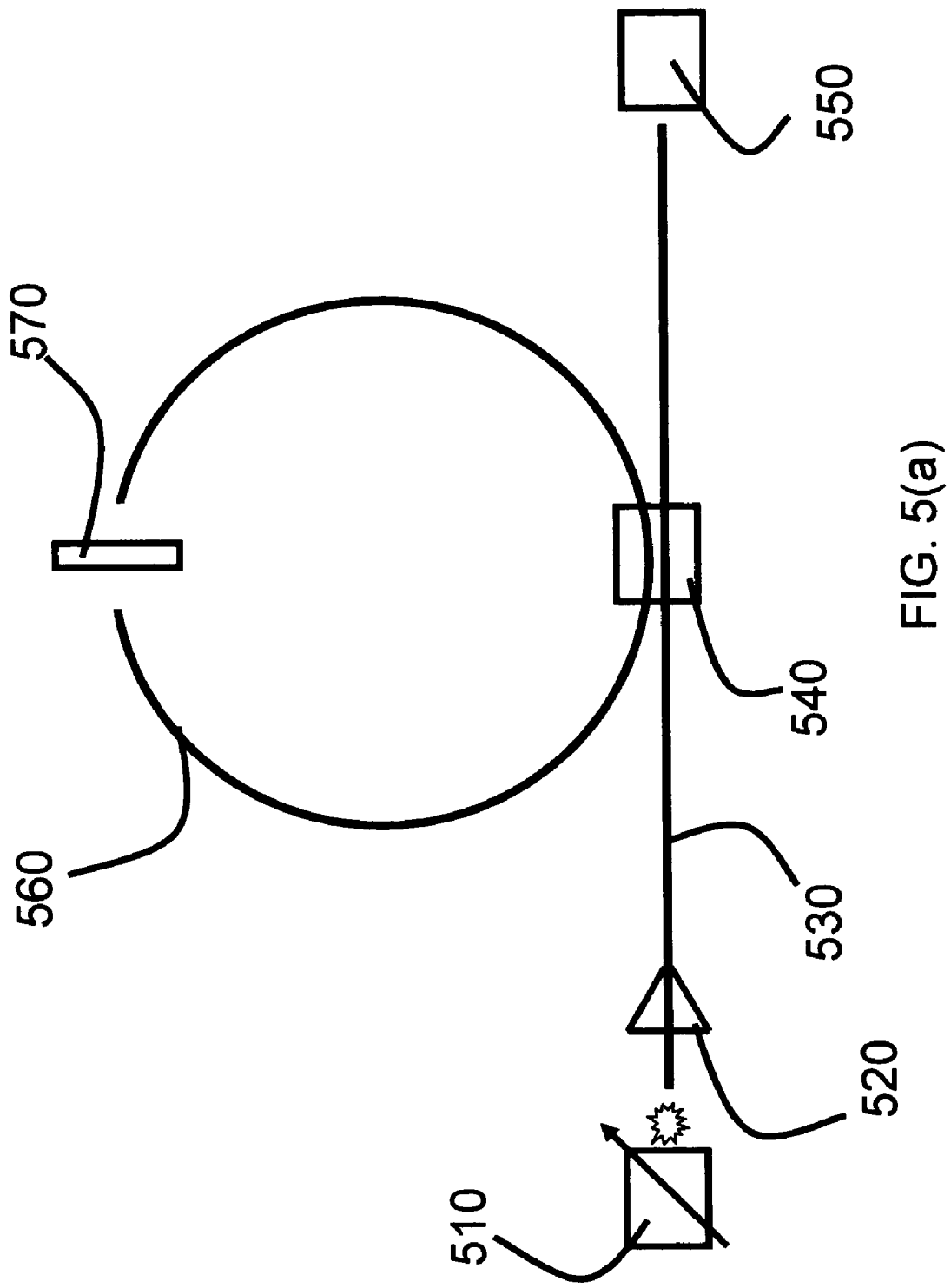
FIG. 5(a) is a block diagram of an apparatus described in Example 1 below.
Figure 5B:
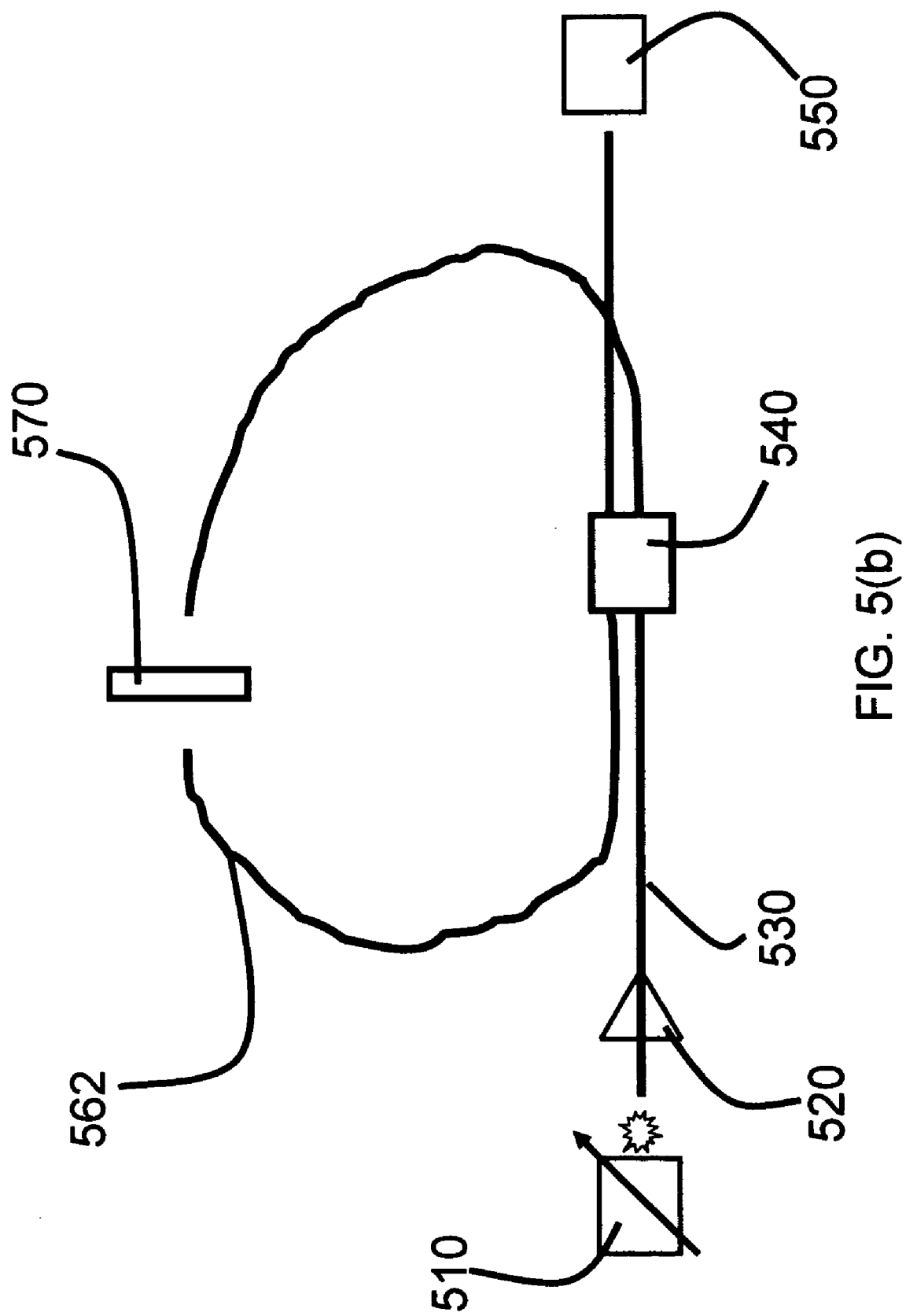
FIG. 5(b) is a block diagram of an apparatus described in Example 1 below.

A sample is placed in the optical path of the resonator. Placement of the sample in the optical path includes absorption by the resonant structure. The light propagating in the resonant structure therefore passes through the sample. This can be achieved in a variety of different ways, for example, such as coupling the light out and back in to the fiber loop using lenses (U-bench), or by directly aligning the fiber ends leaving an air or liquid filled gap in the waveguide structure such that a sample may be introduced in it, or by using inherently porous or hollow waveguide, such as, but not limited to, a porous waveguide, resonator with appropriate openings or a photonic crystal fiber or waveguide. This method derives its highest sensitivity from the narrow linewidth of optical resonances. Extreme narrow linewidth gamma, shown in FIGS. 4(a)-(b), allows the apparatus to determine even small changes in the resonant frequency.

The sensing principle is based on acquiring a spectrum by scanning the wavelength with a tunable laser. The tunable laser can be e.g. external cavity laser, distributed feedback laser etc. It is possible to measure a resonant spectrum throughout the electromagnetic spectrum, in particular from UV to far-IR. Material inserted in the resonant structure will change the characteristics of the spectrum in particular will it change the resonance wavelengths.

The transmission spectrum can be obtained by either placing a detector in the resonant structure, by tapping the light from the resonant structure using a beam splitter and projecting the tapped light onto a detector, or by measuring the transmitted light intensity in the linear part of the resonant structure.

Lasers can be tuned with very high frequencies e.g. GHz frequencies to acquire the spectrum. This technique thus promises to be a very fast technique. Materials with different properties can be inserted into the ring. These material properties allow to design sensors for different other materials or fields. By introducing materials susceptible to magnetic field it is possible to detect the strength of a magnetic field via the magneto-optic (Faraday) effect or determine other magnetic field dependent material properties.

As shown in FIG. 4(c), by tapping the light from the resonant ring using a beam splitter or equivalent structure it is possible to make use of the resonant modes in separate (polarization sensitive) spectroscopic investigations. Should there be two or more modes with different polarization states, then the tapped resonant ring can serve as an effective polarization modulator. By tuning the frequency of the laser (potentially high frequency) over the resonant frequencies of two or more modes it is possible to access light with different, potentially orthogonal, polarization states.

A ring resonator and detection of its resonant modes may be more fully understood through the following examples.

EXAMPLE 1

Example 1 will be described with reference to FIGS. 5(a), 5(b), 6(a) and 6(b). A tunable distributed feedback (DFB) laser diode 510 operating at nominal infrared wavelength of 1.31 μm was coupled into a single mode optical fiber 530 using a single stage coupler (not shown). An inline optical isolator 520 isolates the source from the remaining optical circuit. Using a fiber optic U-bench (not shown) such as Thorlabs, part # FB220-FC, light is passed through a polarizer 610 and a half waveplate (λ/2) 620. The optical fiber ring 560 is closed with a conventional 50/50 coupler 540, such as the Thorlabs, part # SMC11350229U. The light is detected using a conventional InGaAs photodetector 550, such as Thorlabs, part #PDA400. The laser wavelength may be tuned by modulation of the diode current at 100 Hz. For each scan, an intensity spectrum is measured with the photodiode 550 and digitally recorded on a computer (not shown). The tuning coefficient of the laser was previously determined using a conventional wavelength meter as 0.0055 nm/mA (wavelength change/diode current). The circumference of the single mode fiber ring 560 was 1 meter.

Figure 6A:
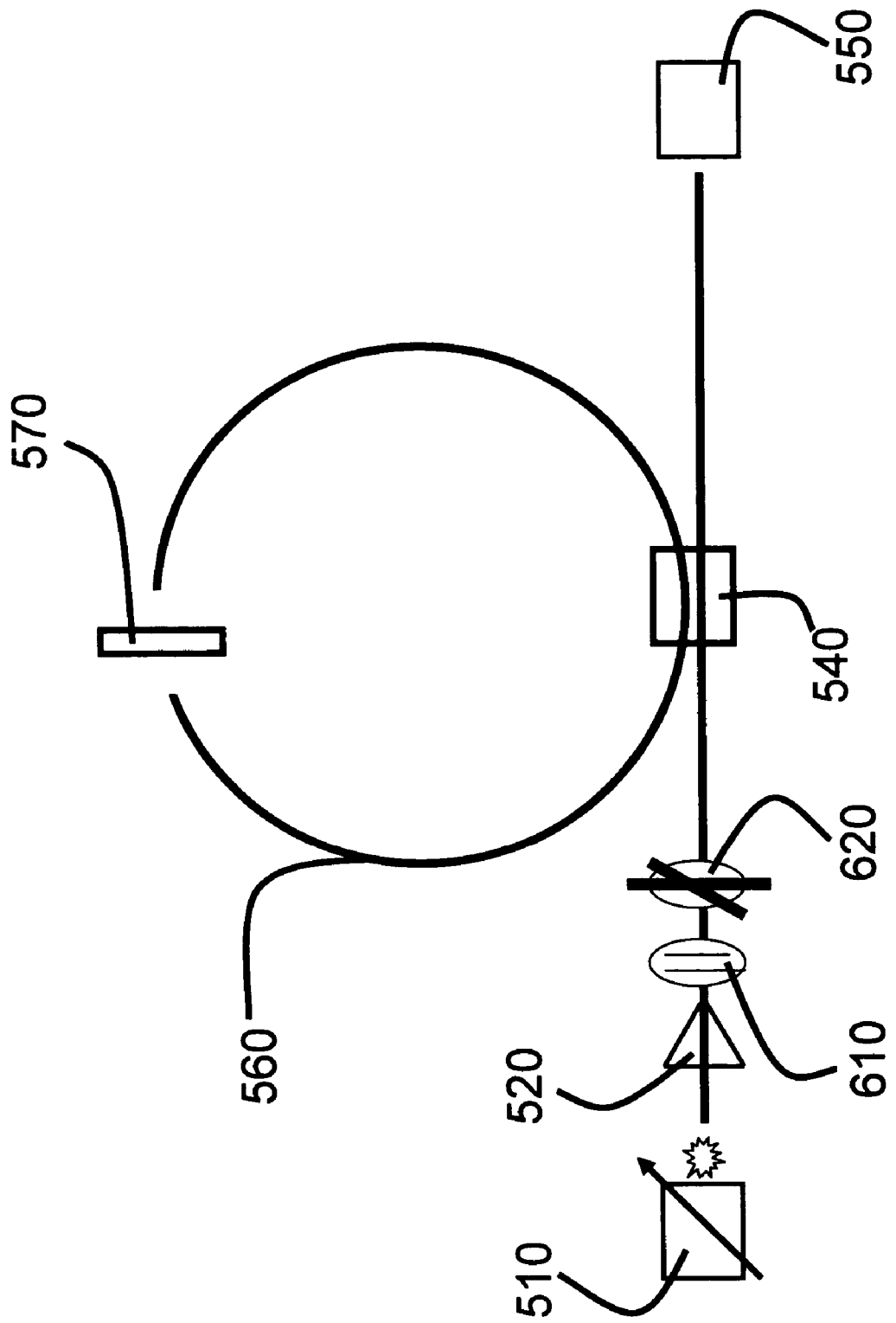
FIG. 6(a) is a block diagram of an apparatus for measuring a refractive index in accordance with a preferred embodiment of the invention.
Figure 6B:
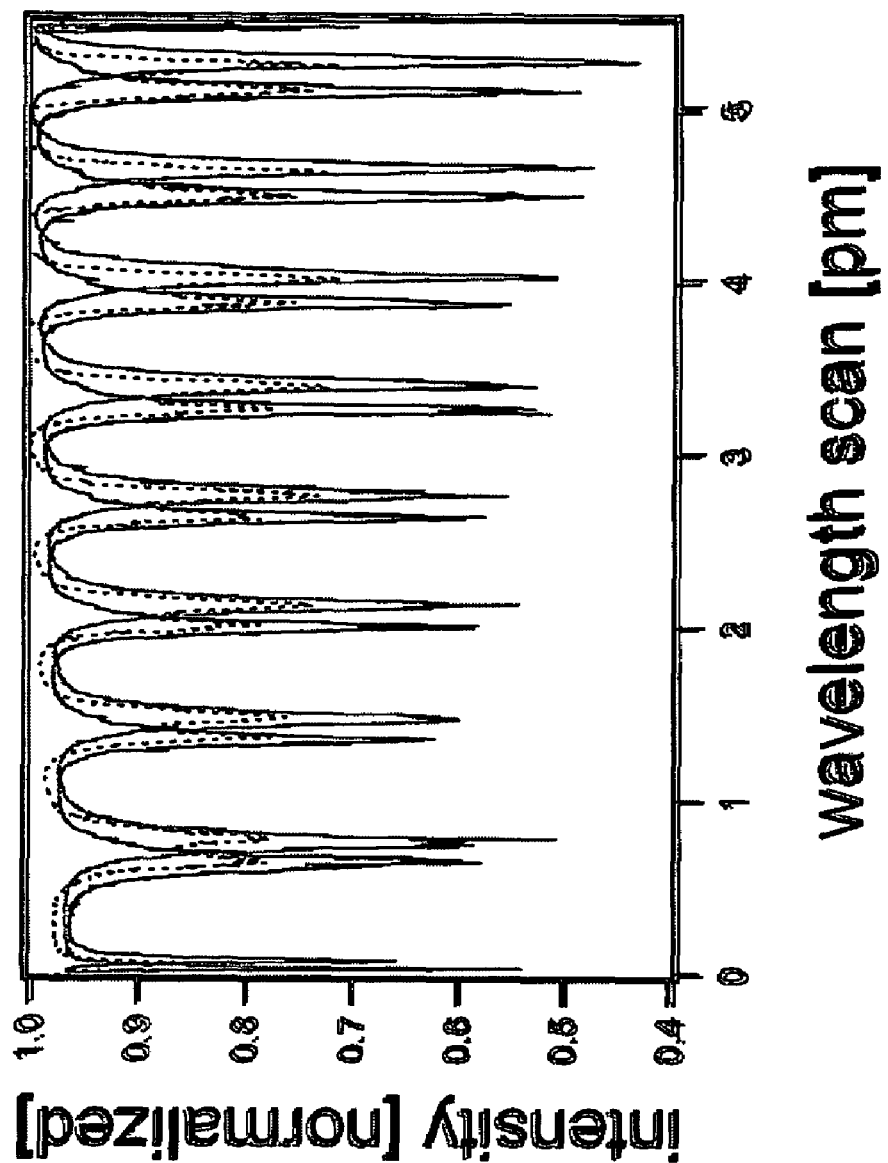
FIG. 6(b) is a diagram of transmission spectra recorded in accordance with a preferred embodiment of the invention.

By turning the half wave plate, it is possible to discriminate orthogonal states of resonant light in combination with a linear polarizer. Transmission spectra were recorded with the photodetector 550 and are shown in FIG. 6b. The transmission spectra show that the excitation of a resonance in the fiber ring is, in this particular case, associated with a drop of the intensity transmitted through the fiber optic circuit at the individual resonance wavelength. As expected from theory, resonances appear periodically in the recorded transmission spectrum. This shows that the resonances were in this case identified as dips in the transmission spectrum. One of the two overlayed spectra is recorded at 0 degree relative angle of the half wave plate with respect to the linear polarizer (i.e. no rotation of the plane of polarization of the light with respect to the axis of the polarizer), the other spectrum is recorded with a 45 degree relative rotation of the half wave plate (i.e. after the half-wave plate the plane of polarization of the light is orthogonal to the axis of the polarizer). The spectra clearly show that different polarization states excite modes that have different resonant frequencies in the ring.

EXAMPLE 2

Figure 7A:
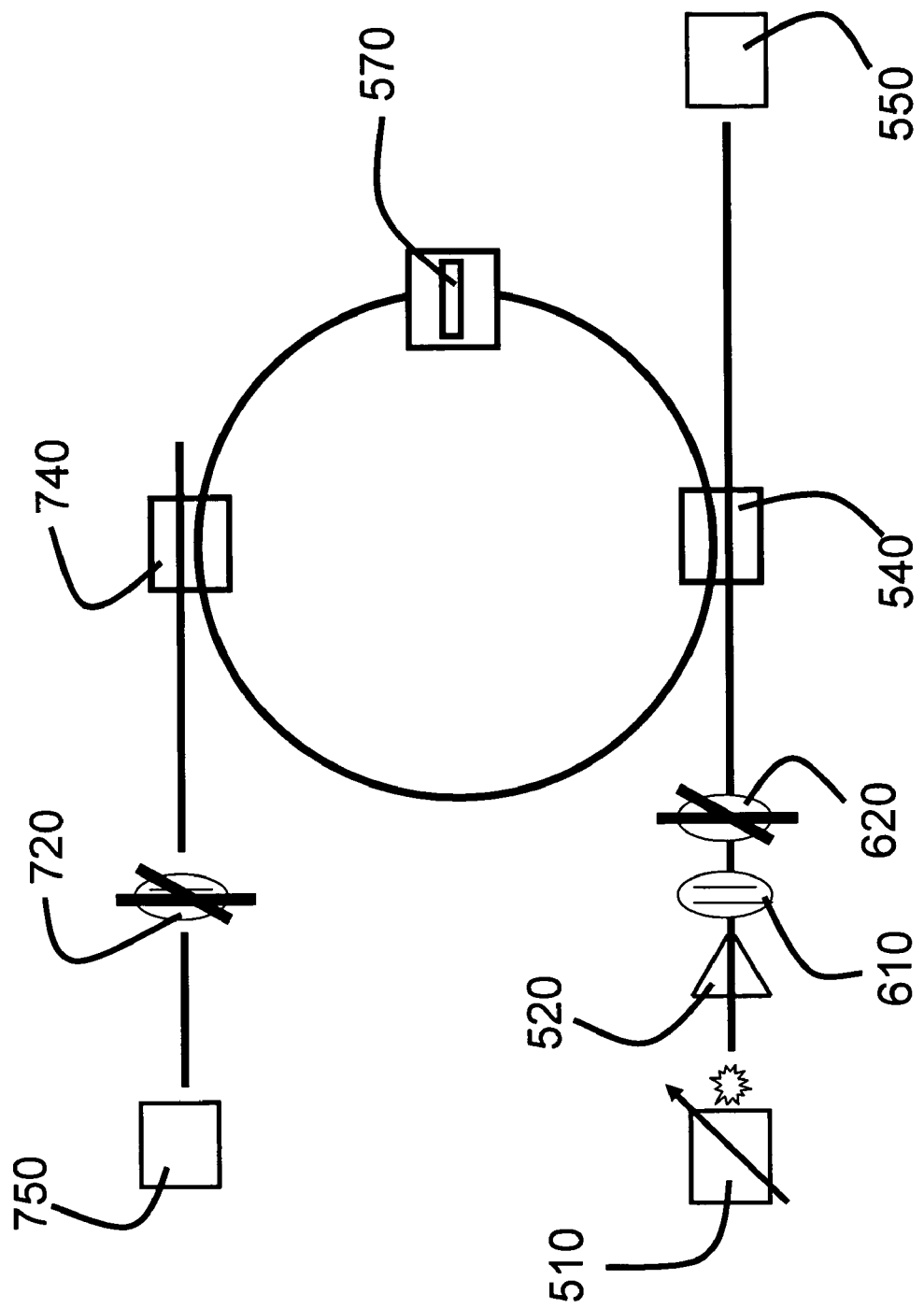
FIG. 7(a) is a block diagram of an apparatus for measuring a refractive index in accordance with an alternative preferred embodiment of the invention.
Figure 7B:
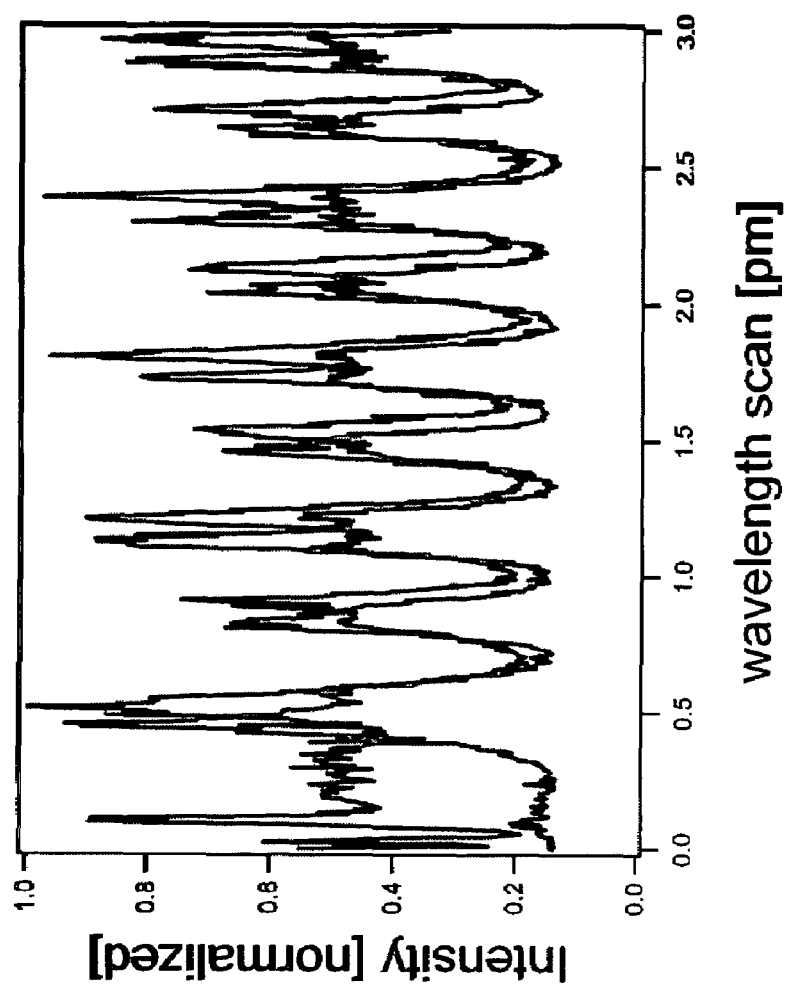
FIG. 7(b) is a diagram of transmission spectra recorded in accordance with an alternative preferred embodiment of the invention.

Example 2 will be described with reference to FIGS. 7(a) and (b). The figures schematically depict an alternate resonant ring structure for the measurement of refractive indices and or the detection of biological and/or chemical agents. It shows that the resonant light can be tapped using a second linear waveguide that is coupled to the resonator. This example directly demonstrates the presence of the two orthogonally polarized light states in the resonant ring. Two different polarization states are analyzed using the polarizer 720. It also shows how two or more resonant structures can be coupled using a common linear waveguide: instead of 720 and 750, the light can be rerouted to a different spectroscopic investigation e.g. another resonant structure. In the apparatus shown in FIG. 7(a), the optical circuit of FIG. 6(a) has an additional 50/50 coupler 740 and an additional polarizer 720. The second 50/50 coupler 740 allows resonant light to be coupled out of the ring. With this modified apparatus, resonances of the ring (see FIG. 7(b)) now appeared as peaks in the transmission spectrum as recorded by the photodiode (detector) 750 at the individual resonance wavelengths. The second polarizer 720 was used to analyze the polarization state of the light coupled out of the ring. The angle of the half waveplate 620 was positioned at 22.5 degree relative angle as compared to the polarizer 610. At this position the two orthogonal modes of the resonant ring are excited at the individual resonance frequencies in one scan of the laser. The polarization state of the light coupled from the ring at the resonant wavelengths was analyzed using the polarizer 720. This resulted in agreement with the data in FIG. 4(b) that there are two orthogonally polarized resonant modes excited in the fiber ring in one scan of the laser diode. One may select each set of polarized modes by turning the polarizer 720 by 90 degree thus analyzing for quasi-transverse electric to quasi-transverse magnetic resonant polarization states of the ring.

The sample may be introduced into the ring-resonator in a variety of ways: e.g. a gap in a waveguide resonator into which a sample may be placed, a fiber 'U-bench' in a fiber-loop resonator, a hollow or porous waveguide or fiber that is part of the resonant ring and that can be filled with a sample, a inherently porous photonic crystal ring resonator etc. Whether the light leaves the fiber or waveguide and travels through free space before it re-enters the waveguide or fiber, or whether the resonator contains a hollow section, it is essential that in all cases resonances are still present, i.e. their spectral signatures are observable at a detector after the sample has been inserted into the optical path of the resonator.

Resonances are a function of the size of the ring (optical path-length), its refractive index (indices) and thus the frequency of the resonances necessarily changes as a sample is introduced into the resonant ring. In order to determine the birefringence of a sample, the present invention makes use of resonant rings that have two (or more) modes with (quasi-) orthogonal polarization states. Optical rotation (circular birefringence) and linear birefringence are observed as relative changes of the resonant frequencies of the modes. The refractive index is determined by the absolute shift of the resonances. The method of the present invention is general, sensitive, and can be described as "all optical" as it requires no moving parts. The method is intrinsically fast: it is mainly limited by the response time of the detector and the speed at which the wavelength of the laser can be changed. Since narrow-linewidth lasers can be tuned at rates of more than 1 GHz, the present invention allows for ultra-fast refractive index, birefringence, and optical activity measurements.

As shown in FIG. 8(a), a sample cell 810 may be introduced into the fiber loop 560 by connecting a fiber optic U-bench 820 in the ring 560. For this purpose, the optical fibers of the ring 560 and U-bench 820 could be joined by using standard FC/PC connectorized fiber ends (not shown) or by directly fusing two optical fibers using a conventional fusion splicer (e.g. Fitel S148) (not shown). The U-bench 820 makes it possible to insert a sample into the beam as it traverses 'free-space,' which is denoted by the dotted line 830 in FIG. 8(a). The sample 810 can for instance be a liquid in an appropriate cuvette. A top view of the sample 810 is shown in FIG. 8(a) as item 810a. Using a standard 2 mm path length quartz glass optical cuvette, the resonant frequencies will change as liquids with different refractive indices are filled into the cuvette.

Figure 8B:
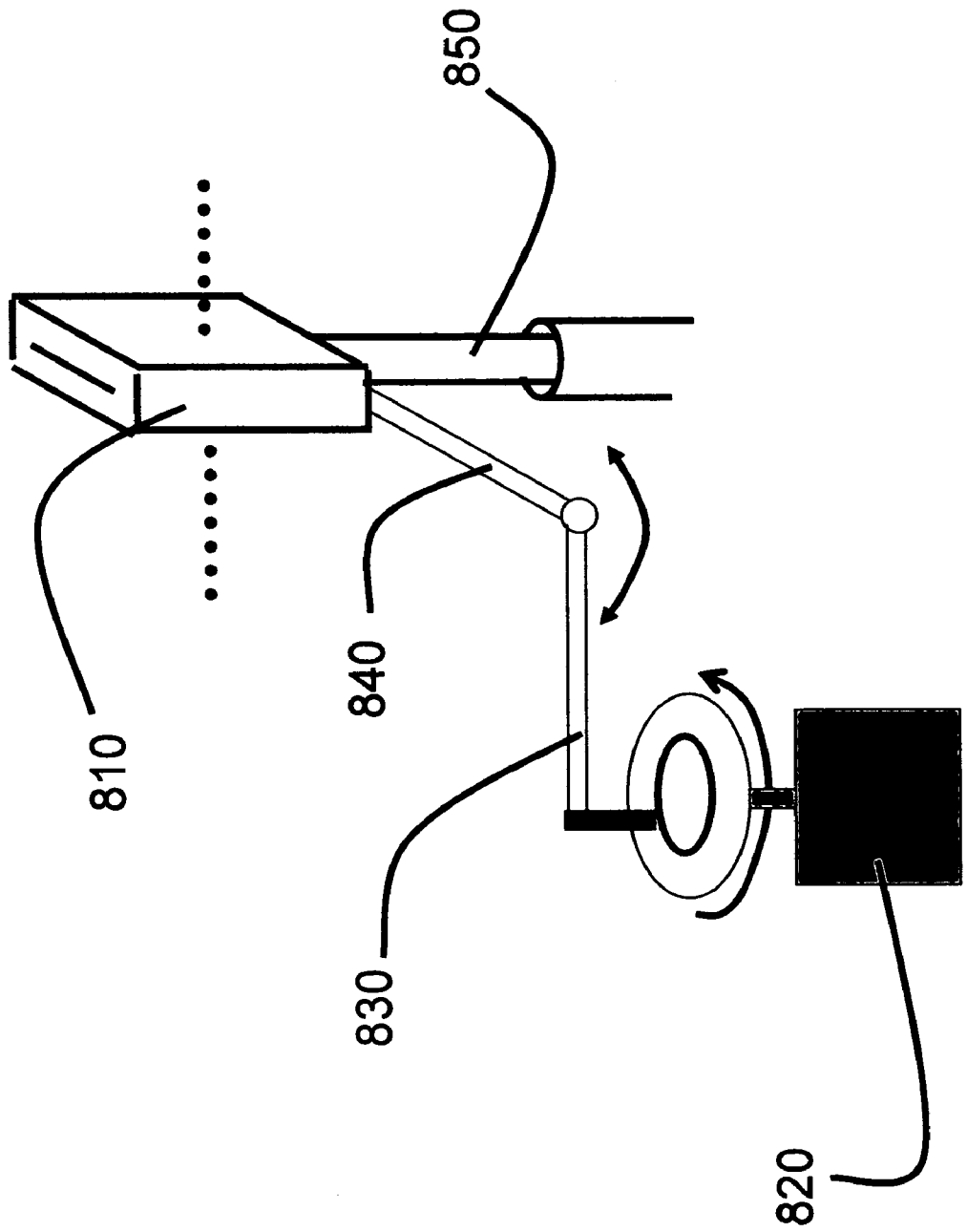
FIG. 8(b) is a block diagram of a motor apparatus for rotating a sample cell in the embodiment of FIG. 6(a).
Figure 8D:
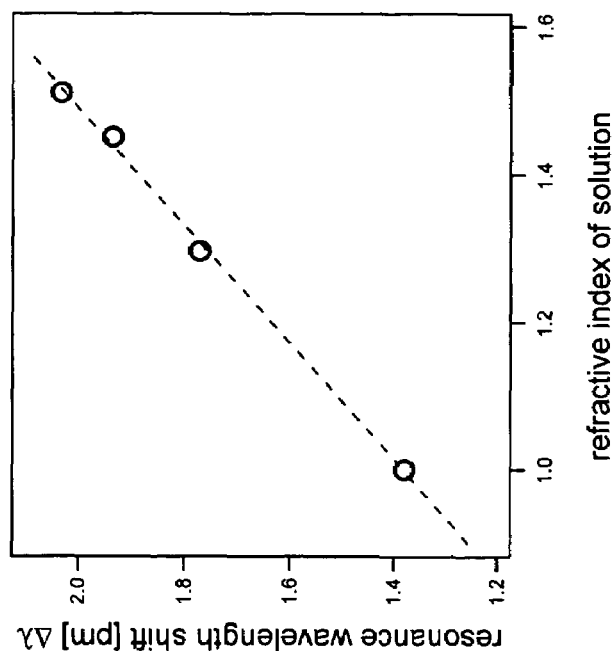
FIG. 8(d) is a graph of resonance wavelength shift versus a refractive index of a solution.
Figure 8C:
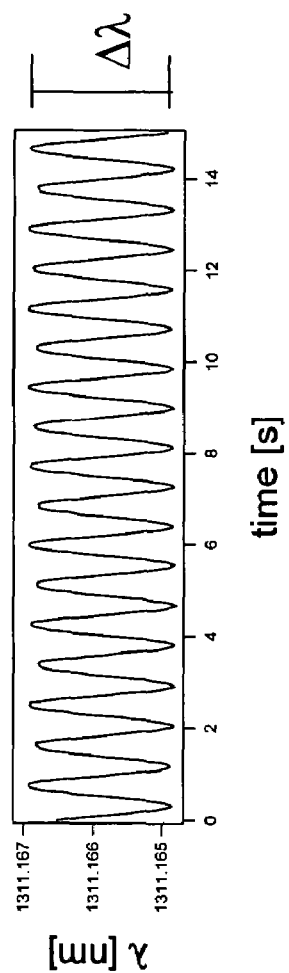
FIG. 8(c) is a graph demonstrating how a resonance wavelength changes with pathlength.
Figure 9:
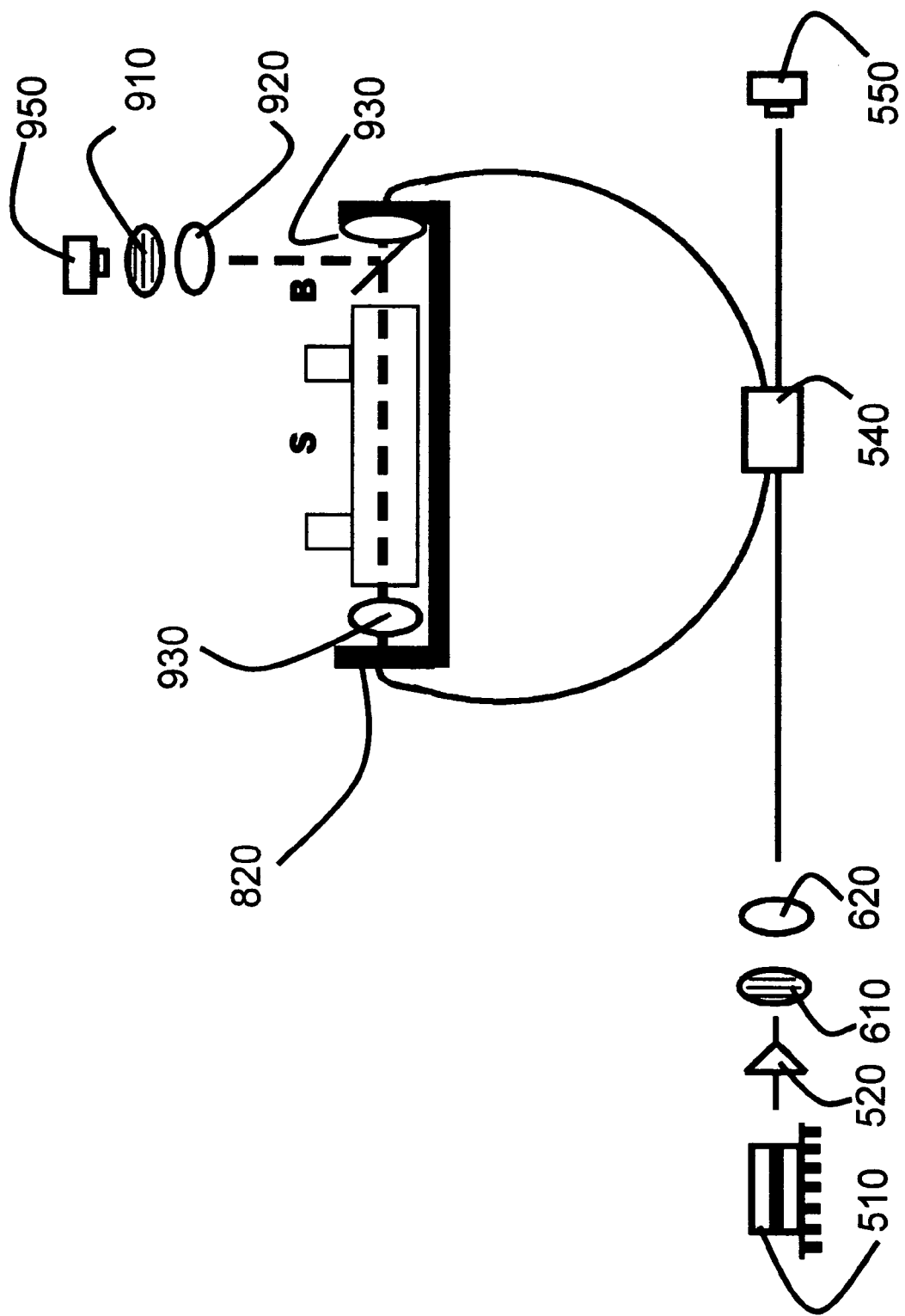
FIG. 9 is a block diagram of an apparatus for chiral discrimination in accordance with a preferred embodiment of the invention.

Rotation of the cuvette from position 810, 810a about an axis perpendicular to the light-path to position 812, 812a causes an increase in the distance the light-beam travels through the sample (here quartz cuvette filled with liquid). The distance through air is correspondingly shortened. As shown in FIG. 8(b), a motorized stage having a motor 820, arms 830, 840 and a support 850, can be used to sinusoidally rotate the cuvette by a few degrees about the normal such that the path-length of the cuvette increased up to 15 µm. Measurements of the periodic wavelength shift associated with this periodic change of path-length correlate with the refractive index of the solution (FIGS. 8(c) and (d)). From this data, one can estimate the sensitivity of the method. In one particular measurement, the refractive index contrast Δn was 0.5101, i.e. the measurement of the sample cell filled with a liquid of n=1.5101 from Cargille Lab., Series A at 1310 nm compared with that of the empty cuvette, i.e. air, n=1.0 (first and last data points in FIG. 8(b)). The associated wavelength shift was about 1.6 pm.

The linewidth of the resonant line is on the order of 0.1 pm. With the given noise in this preferred embodiment, the wavelength of a resonance line with an accuracy of ~$1/10^{th}$ of its linewidth. The signal to noise ratio (S/N) for this measurement was thus determined to be about 150. Extrapolating, the technique can readily sense an optical-length, which may be defined as either the refractive index change times path-length, or the change in path-length times refractive index, of 100 nm with a S/N=2. Hence, one can estimate that the preferred embodiment makes it possible to detect refractive index changes of $10^{-5}$ in a 1 cm standard cuvette. With this level of sensitivity, the present invention makes it possible to determine (1) refractive indices with an accuracy of commercial refractometers; (2) linear birefringences of thin films; and (3) optical activities.

However, the present invention is based on a fundamentally different principle of measurement compared to other equivalent established techniques, namely, the present invention measures refractive index changes and or birefringence in the frequency domain in a resonator. Hence, it can be faster than other methods, requires no expensive optics, may be fiber based, has no moving parts, can easily be miniaturized.

Additional sensitivity of the apparatus and method of the present invention can be achieved by modifying the apparatus and method in a variety of ways. For example, reduction of the cavity size, e.g. the circumference R of the ring resonator, increases the wavelength-shifts due to perturbation of the total ring size (the wavelength-shift is inversely proportional to R). Hence it follows that the sensitivity of the measurements (and hence the above estimates of the sensitivity of the technique) can readily be improved by one or even several orders of magnitude with ring-resonators with smaller circumference. These could for example be fabricated as race-track waveguides or as low-loss photonic crystal ring resonators. Further, one may improve the linewidth of the resonant modes. By decreasing the insertion losses of the U-bench (or similar structure) e.g. by introducing anti-reflection coatings, better beam alignment etc. it is possible to increase the linewidth of a given ring resonator. Additionally, one may eliminate losses due to absorption as well as strain and stresses in the fiber-loop and/or waveguide structure will also sharpen the resonances. Also, the resonators or waveguides can be manufactured such that their resonant modes have favorable, e.g. orthogonal linear or circular polarization states.

The present invention may further be applied to measurements of other optical properties such as linear birefringence and circular birefringence. For example, as the wavelength of the laser is tuned two (or more) distinct (quasi-) orthogonal modes can be alternately excited in appropriate waveguides or ring resonators that support such modes. The modes preferably are predominately linearly (or circularly) polarized with orthogonal polarization states at the location the sample is introduced into the resonator. This may arise naturally due to the optical properties of the resonator as in an asymmetric waveguide structure, or can be achieved with strain birefringence in the case of a single-mode optical fiber loop resonator. In addition, waveplates and polarizers may be used to affect the polarization states of the modes at the location of the sample, e.g. should the modes be circularly polarized, and then the right- and left-circular polarized beams can be converted to linear polarized light with orthogonal polarization states by way of a quarter-wave plate and vice versa.

As the frequency of a narrow-linewidth laser is scanned, the two (or more) non-degenerate modes are excited alternately and are observed in the transmission spectrum at the detector as peaks or troughs, i.e. enhanced or reduced transmission, respectively. A sample that exhibits linear birefringence is characterized by different refractive indices that are along two directions (axes) that are orthogonal to each other. Should the sample be placed into the resonator, and should the polarization states of the modes be parallel to the axes of the sample, then their resonant frequencies shift by different amounts. The spacing between the two resonant modes as a function of frequency therefore changes upon the introduction of the sample. Determination of the relative shift in resonant frequencies constitutes the measurement. In addition, the birefringent sample may be rotated around its optical axis to determine the orientation of the fast and slow axis of the birefringent sample.

A preferred embodiment for measurement of circular birefringence is the same as in the linear birefringence measurements except the modes need to be (or have components that are) left- and right-circularly polarized. The circular polarization may arise due to the structure and geometry of the resonator or may be achieved by strain birefringence (twist) etc. Alternately, if at the location the sample is introduced, the resonator has modes that are predominately linearly polarized with orthogonal polarization states, then the introduction of a quarter waveplate will render these modes circularly polarized with opposite circularity. Hence, the optical activity of a chiral liquid or amorphous solid can be determined. The relative shift in resonant frequencies is a function of the enantiomeric excess in the case of an optically active liquid.

Application of a magnetic field along the propagation direction of the light through the sample in the resonator will give rise to the Faraday Effect. The concomitant circular birefringence then may be measured.

An alternate embodiment for the measurement of refractive indices and or birefringences and any possible application to biological and or chemical sensing is the observation of spectral changes in the transmission spectrum of the ring resonator or equivalent structure in the presence of a sample introduced in the resonator's optical path.

An alternate embodiment of the technique is based on the measurement of the resonator's ringdown in order to determine refractive indices or birefringences of appropriate samples including biological and or chemical agents that are introduced in the resonator's optical path.

EXAMPLE 3

Figure 10A:
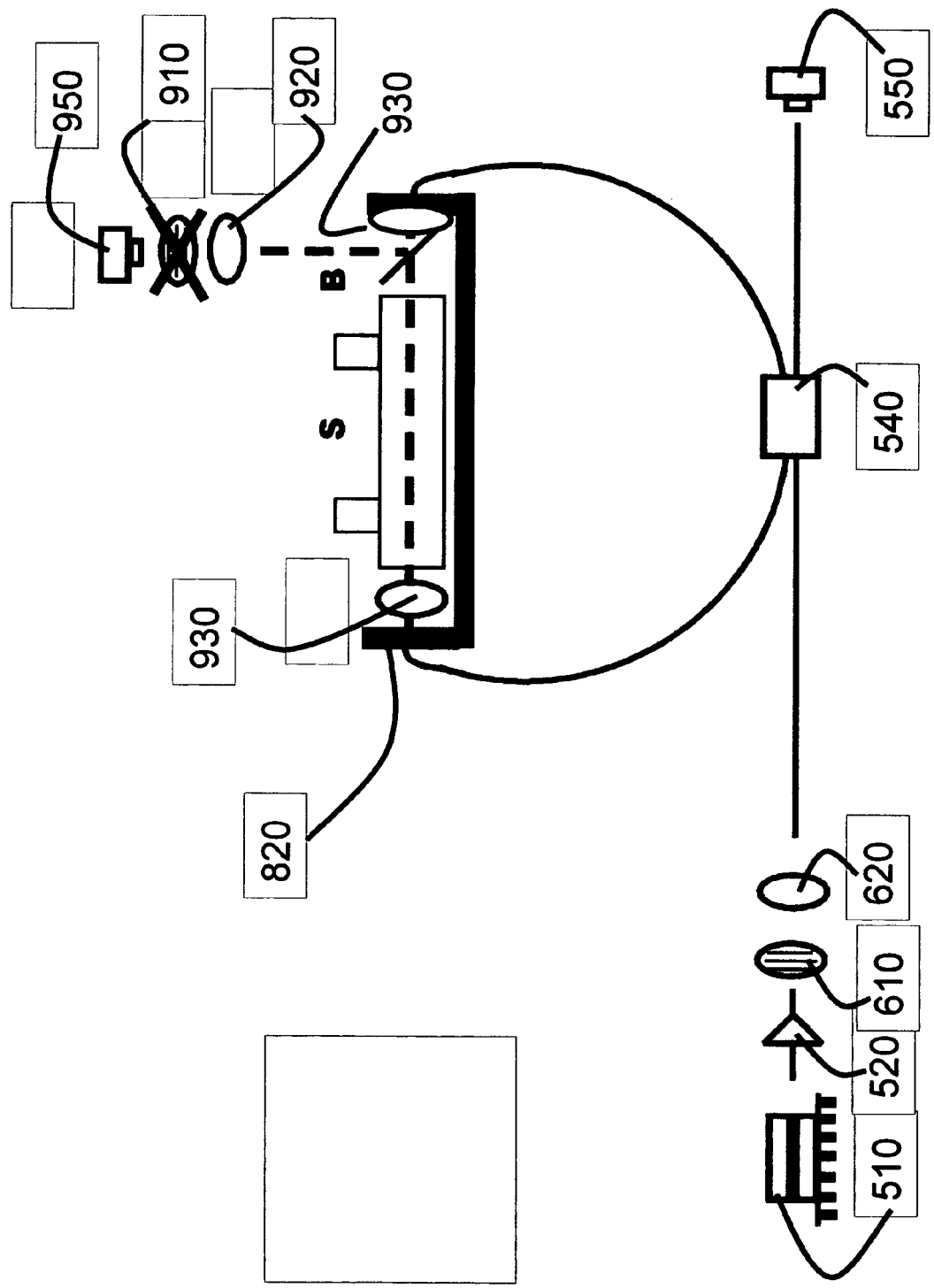
FIG. 10(a) is a block diagram of an apparatus for the measurement of enantiomeric excess and or the optical activity of an optically active solution in accordance with a preferred embodiment of the invention.

A sample cell of 10 cm path length was introduced into a resonant ring of ~60 cm total circumference FIG. 10a. The sample cell was first filled with R-limonene. A transmission spectrum of the resonant modes was recorded using a tunable distributed feedback laser 510 with a nominal wavelength of 763 nm. The half-wave plate 620 was positioned so that two modes were excited simultaneously.

Before taking the measurements, the light is analyzed with the detector 950. A quarter waveplate 920 is positioned in the beam in front of a linear polarizer 910. By turning the polarizer by 90 degree we can select for one of the two orthogonal set of resonant modes (dark and light solid lines in FIG. 10b). By adjusting the quarter waveplate 930, the resonances were changed so that the two modes analyzed by 910 correspond to left and right circular polarized light respectively. The two modes with orthogonal polarization states can be observed as peaks by detector 950 or as dips by a photodetector 550.

For the subsequent discussion we will use the spectra detected by 550. Preliminary data further suggests that the modes had a circular polarization component as a relative shift in the resonance frequencies was recorded as the S-enantiomer of limonene was introduced into the cuvette. Comparing the R-limonene with the racemic mixture, R/S-limonene, we observe in the transmission spectrum that the relative spacing of modes with opposite circular polarization changes. Such a relative shift of the resonance frequencies is measure of the liquid's circular birefringence. The magnitude of relative wavelength change $\Delta\Delta\lambda$ is in accord with theoretical estimates.

Figure 10B:
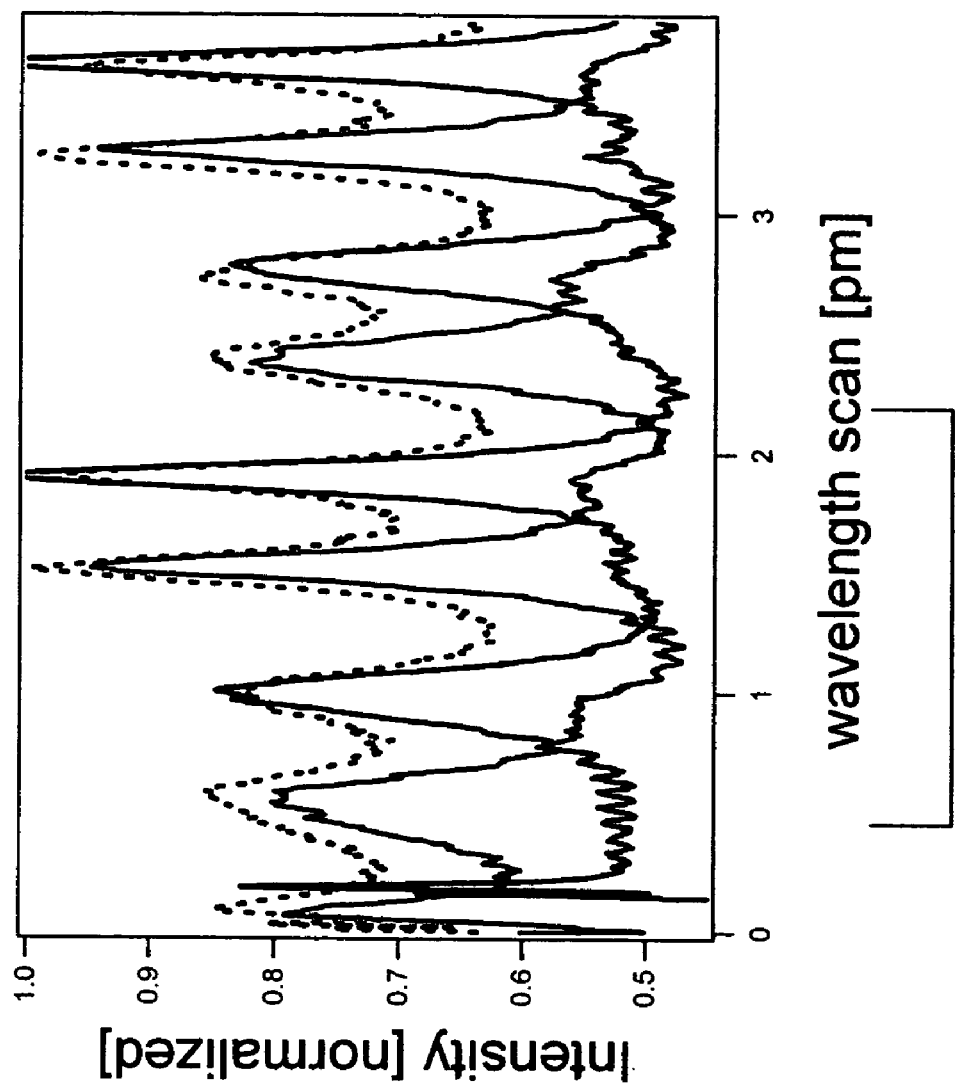
FIG. 10(b) is a diagram of spectra recorded in the resonant mode by coupling out some of the light in the resonant ring (tapping) in accordance with a preferred embodiment of the invention.

FIG. 10 (a) shows one embodiment of the invention which allows to measure enantiomeric excess of an optically active liquid. In addition to the sample cell S, here a 10 cm liquid cuvette, a beamsplitter B and a quarter waveplate 930 is introduced into the resonant ring. The light from the beamsplitter B is projected through another quarter waveplate 920 and a linear polarizer 910 onto a photodetector 950. A tunable laser 510 operating at 763 nm nominal wavelength is coupled into the linear waveguide. The source is optically isolated with an optical isolator 520. The light is further polarized through a linear polarizer 610. The axis of polarization can be rotated using a half waveplate 620. A photodetector 550 records the transmitted intensity through the linear waveguide. A variable ratio coupler 540 is used to couple light between linear waveguide and resonant ring. The half waveplate 620 and the quarter waveplate 930 are adjusted so that the light passing through the beamsplitter and into the sample cell is circularly polarized. 930 and 620 are adjusted so that both left and right circular polarized resonant modes appear as peaks or dips in the spectra recorded by the detectors 950 and 550 respectively. We confirm the presence of left and right circular polarized resonant modes with 920 and 910. Since we can select for one set of resonances by turning the polarizer 910 by 90 degrees this proves that the two orthogonal set of resonances of the ring are left and right circular polarized light. As the frequency of the laser is scanned the resonances alternate such that a left circularly polarized mode is followed by a right circularly polarized mode. Optically active R-limonene is first introduced in the sample cell S. In what follows a volume of the enantiomer (S-limonene) is added to the R-limonene until the solution is no longer optically active, i.e. is a racemic mixture. The percentage of S-limonene added (0-50%) can be correlated with a change of the relative spacing of the left- and right-circularly polarized resonant light modes FIG. 10b. FIGS. 11(a) and (b) show plots of the resonance spacing (left circularly polarized light, lcp and right circularly polarized light, rcp) with respect to the percentage S-limonene added to the R-limonene. Both solutions have the same optical purity. FIG. 12 shows that two independent measurements of the slope of the curve are reproducible and are related to the change of refractive index with enantiomeric excess (volume of S-limonene titrated into a volume of R limonene). The change is indicated in the figure as a change in the circular birefringence as a function of the enantiomeric excess.

In the following embodiments of the present invention, distributed feedback telecommunication lasers with typical center wavelengths at 763 nm, 1310 nm and 1555 nm were used. The scan range was on the order of one nanometer. Alternative tunable sources are such as external cavity lasers (e.g. at 633 nm) may be used. At resonance, the measured light transmission through the bus waveguide will drop in amplitude due to phase shifts that occur when coupling in and out of the resonator and the interference of the light that has coupled out of the ring resonator and therefore interferes with the light in the bus-waveguide. The resonance frequencies are identified by the minima (typically lorentzian dips) in the transmission spectrum. By changing the coupling parameters it is even possible to achieve critical coupling where no light is transmitted through the bus waveguide on resonance. Resonators operating in the regime of critical coupling find application as add-drop filters, as means to delay a pulse, filters, etc.

The resonance frequencies of the fiber-loop resonant ring depend sensitively on the ring parameters such as size, strain, twist, refractive index etc. The measurement of the resonance frequencies (and other transmission characteristics) monitor changes in these parameters and can be used for sensing applications. For this purpose, a resonant ring in itself can be used as a sensitive instrument to monitor changes of any of those parameters or to measure perturbations that affect these variables. Strain and temperature sensors have been proposed and built.

The present invention incorporates a novel method to access the light propagating in the ring structure for optical measurements. The ring structure does not have to be continuous in order to maintain narrow linewidth resonances (FIG. 13; FIG. 15). In fact, the light can be propagated free space using e.g. fiber ports for coupling in and out of a fiber loop. Despite of the optical losses associated with such an open ring structure the resonances remain surprisingly sharp (FIG. 15). One can even introduce a beam splitter with almost no noticeable effect on the linewidth (much smaller than 10%).

The narrow linewidth ring-resonator containing one or several gaps in which the light traverses free space and/or through a sample volume opens up a host of possibilities for optical devices. The light beam can now propagate through a sample volume for measurement and sensing applications. Polarization sensitive measurements are possible since orthogonally polarized light modes can be present in the resonator (e.g. quasi-TE and quasi-TM). Optional waveplates inserted in the gap make it possible to manipulate the state of polarization of the light. The interaction of the light with the sample material will lead to a phase shift which can be detected in the frequency domain. For linear polarized resonant modes this allows one to measure linear birefringence of an anisotropic solid sample, or thin-film. Circularly polarized modes are required to measure the circular birefringence of an optically active liquid. Ring resonator structures that support linear and circularly polarized light modes may be built. The (left and right) circularly polarized light modes are used to determine the enantiomeric excess in a chiral solution. The scaling of this ring resonator sensor is interesting since the sensitivity does not depend on the size of the ring structure as compared to other polarimetric techniques that depend linearly on the path-length through the sample. This suggests that the ring structure can be micro-fabricated without loss of sensitivity towards the detection of an analyte if the sharpness of the resonances remains constant. Such resonant ring sensor elements are ideal components for the analytic part of a lab-on-a-chip device.

A ring that constitutes a gap in-line with the resonant light path can be an extremely sensitive detector for perturbations of the gap length. One or several gaps can be included in a resonant structure and could be applied for ultra-sensitive strain and distance measurements, for example when mounted on the tip of an atomic force microscope (FIG. 23). The possibility for making a ring resonator structure on the micro-scale allows for integration with many other MEMS (micro-electro-mechanical structures) or lab-on-a-chip devices. When monitoring the gap-length change of a ring resonator it is important to note that the sensitivity of the measurement will increase with smaller overall ring-size sizes of the wave guiding structure. A ring resonator that is used for distance measurements is thus more sensitive the smaller the ring structure is, provided the same sharpness of the resonances is maintained.

The cavity can contain one (or more) reflecting surface(s), e.g. mirrors, (FIGS. 16-22). This is possible by introducing a fiber optic circulator in the resonant ring. The light from one port of the circulator is reflected from a surface and channeled back into ring. A sample surface can thus be raster-scanned in the xy plane similar as in a near field optical microscope. The end of the fiber of the circulator which is probing the surface can be modified in different ways. Different tapers and metal coatings can be applied in order to maximize the xy resolution of this device. The z-sensitivity (distance from the surface) is very high since it can be measured from a frequency shift of the narrow linewidth ring resonator: any variation of the height of the scanned reflecting surface will lead to a gap-length change of the ring resonator. Again, the scaling of such a scanning device is extremely interesting since it promises to become more sensitive for smaller waveguiding structures.

The ring structure can be completely avoided by using a one dimensional cavity (FIGS. 21 and 22). Such a one dimensional cavity is a simple fiber coupler with reflecting surfaces at both ends. One of the surfaces could be a raster scanned sample surface.

In general, an open ring (with or without reflecting surfaces) is a convenient and sensitive optical means for measuring phase changes in the frequency domain. A phase change occurs for example when the size of the ring or gap changes thus shifting the resonance frequency. Such a phase change can be induced not only by dimensional changes, but also by other physical effects such as e.g. surface plasmon resonances. Although here the scaling and sensitivity is determined by different expressions (see analysis below). In a specialized setup it is possible to monitor the phase change associated with a surface plasmon resonance perturbed by molecular binding using an open resonant ring structure (FIG. 27-30).

An open ring resonator that supports surface-plasmon resonances can be realized by reflecting the light in the ring off a metal coated prism (Kretschman configuration, FIG. 26). More conveniently it is also possible to partially remove the cladding of a fiber loop resonator onto which a thin metallic film is directly evaporated (FIG. 29-30). It is possible to choose a wavelength range where an optical resonance and a surface plasmon resonance can be excited simultaneously. Molecules binding to the metal surface will sensitively alter the phase of the SPR and thus also the phase of the optical resonance. In another embodiment, part of a resonant fiber loop can be tapered and a metal film is evaporated on the tapered region of the fiber where a SPR is excited. The technique can be combined with high-resolution lateral raster scanning to realize a scanning resonant ring SPR microscopy.

The shift of the resonance frequency is a function of the effective total optical size of the ring resonator and can thus be used to measure or monitor changes in the length of the gap(s). Thereby it is possible to measure the surface profile of a reflecting surface, or monitor changes of the gap length which may be caused by an external perturbation such as changes in temperature, pressure, strain, vibrations, etc.

In one embodiment of the invention the waveguide that forms the ring resonator changes its effective size due to an external perturbation. The waveguide itself may be made from a material that is flexible and that can be expanded or contracted due to an external influence such as a strain. The ring resonator may contain one or more variable gaps—where light leaves the waveguiding structure and travels a certain path length outside that waveguide, for instance through air. (e.g. FIG. 13, 23)

In another embodiment the ring-resonator includes a reflecting surface. The variable gap is located between the reflecting surface and the waveguiding structure (FIG. 16). A ring resonator can accommodate a reflecting surface by:

1) Terminating the end of a straight waveguide with reflecting surfaces (FIG. 22). The state of polarization in such a linear resonator can be controlled with suitable polarization optics in the optical path. The variable gap is located between the end of one waveguide and the reflecting surface.

2) Including an optical circulator in line with the ring resonator. One arm of the circulator is used to scan the surface and propagate the reflected light back into the ring structure (FIG. 14). For this purpose the fiber end(s) that probe(s) the surface can be terminated with a fiber port (FIG. 14), a fiber port and an objective (FIG. 16), a tapered fiber or a tapered metal coated fiber (FIG. 17), two fiber ports and an objective (FIG. 19), a cleaved fiber or any number of optical, mechanical, or electrical elements.

Samples that are not reflective by themselves, such as biological tissue, organisms, biomolecules (DNA, proteins), bacteria, viral particles etc. may be coated with a reflective coating (similar sample preparation as for electron microscopy) and placed on a surface such that the surface relief of the samples can be scanned and monitored by the device.

The dimension of the gap (length) in all of the above mentioned embodiments can be measured and monitored as any change in the gap dimension, $\pm \Delta l$, also changes the size of the ring-resonator and thereby its transfer characteristics. In particular, a change $+\Delta l$ relative to a total size L (which includes the unperturbed gap size l) gives rise to a shift $+\Delta\lambda$ of the resonant wavelength $\lambda$ (e.g., FIGS. 13, 14, 20-23) according to:

$$\frac{\Delta\lambda}{\lambda} = \frac{\Delta l}{L}. \quad (1)$$

(Note: For those embodiments that contain a reflecting surface (e.g. FIGS. 14, 16, 17, 19, 20 and 22) the total path-length L changes by $\pm 2\,\Delta l$ such that Eq. (1) becomes:

$\Delta\lambda/\lambda = \pm 2\,\Delta l/L.$)

As is evident from Eq. (1), larger shifts arise in ring-resonators that have shorter total path-lengths L. The linewidth of the resonance should be small to increase the resolution of the ring-resonator. Such resonant structures are thus ideal sensing elements in micro- or even nanofabricated devices.

The detection of phase changes of the reflected light—e.g. associated with a surface plasmon resonance (FIG. 26-30)—does not entail a change in the dimension of the gap. However, it nevertheless changes the resonance frequency of the associated mode as the change in phase is equivalent to a change in path length. If the phase of the reflected light changes by an amount, say $0<\Delta\phi<\pi$ for p-polarized due to a surface-plasmon resonance [3], then the associated mode will experience a change in the resonance frequency.

The phase changes that s- and p-polarized light experience upon reflection from the surface may be measured and monitored with our invention. The relative change in phase of the reflected s and p polarized light causes the resonance frequency of their associated modes in the resonator to change. In particular near the surface plasmon angle, the phase change of p polarized light is different from s polarized light and the relative spacing between the modes (the difference in their resonance frequencies) changes as the angle of incidence of the light is varied over a (typically small) angular range near the surface plasmon angle (FIG. 27). The angle of minimum reflectance as well as the phase is of the p-polarized versus s-polarized light is particularly sensitive to any material, liquid, solid, or gaseous that is in contact with the evanescent field of the surface plasmon wave (FIG. 27; as in standard surface-plasmon spectroscopy). Any analyte that experiences the evanescent field of the SPR wave (FIG. 27) will give rise to a change in phase. The phase change caused by the presence of any such analytes can be determined from a change of the resonance frequency of a p-polarized resonant mode. As an example, molecules binding to the metal surface will lead to a phase change, such as a monolayer of bound proteins that could be detected by this method.

This invention details how the phase change can be monitored and measured, and how the ring resonator may be used as a sensor that incorporates a surface plasmon resonance, e.g. FIGS. 27 and 28a, b depict a possible embodiment that is used for a biological sensing application. Phase images of the surface plasmon resonance are possible when the surface is scanned laterally (FIG. 15a).

Inclusion of a sample in a gap of fixed length gives rise to changes in the resonance frequencies. Introduction of a sample with refractive index $n_s$ into the ring resonator will cause a wavelength shift of the resonances relative to the reference medium with refractive index $n_0$, which may for instance be air:

$$\frac{\Delta\lambda}{\lambda} = \frac{n_s - n_0}{n_{eff}} f, \qquad (2)$$

where f is the fraction of the total ring circumference that contains the optically active sample. $n_{eff}$ is an effective refractive index used to describe the entire fiber loop resonator in the presence of the reference medium and corresponds to the round-trip phase $2\pi n_{eff} L/\lambda$ acquired by a resonant mode at the wavelength $\lambda$, where the circumference (fiber and free space part) is L.

Resonant modes with differing polarization states may be used to generate circularly polarized modes which are sensitive to chirality. A wavelength shift that is equal in magnitude and opposite in sign for the two circularly polarized modes is a direct function of the liquid's circular birefringence, and hence its optical activity. Of particular interest are thus relative changes in the resonance wavelengths of a pair of left- and right-circularly polarized modes centered at $\lambda=|\lambda^{(-)}-\lambda^{(+)}|/2$:

$$\left|\frac{\Delta\lambda^{(-)} - \Delta\lambda^{(+)}}{\lambda}\right| = \frac{n^{(-)} - n^{(+)}}{n_{eff}} f, \qquad (3)$$

where any common mode noise is automatically eliminated. It is also seen that the equation describing optical activity in a ring-resonator is independent of the actual dimension of the ring. For a given finesse and a given fraction f, a reduction in the size of the ring does not lead to a loss of sensitivity. This is in contrast to all conventional polarimetric techniques.

FIG. 14 shows an experimental arrangement consisting of a fiber loop 1112 of total length L=2 m coupled to a bus waveguide 1114 using a variable ratio coupler 1116. A free-space beam (gap) is part of the ring resonator using a fiber optic circulator, a fiber port and a reflecting surface (mirror) 1200. the reflecting surface 1200 may be simply a reflecting surface, may be a reflecting surface with surface features such as in shown in FIG. 14a, or may be any opaque sample pattern with varying transmittance or reflectance.

FIG. 15 shows a transmission spectrum acquired by coupling a tunable distributed feedback laser of 1550 nm nominal wavelength (Anritsu GB5A016) into one end of the bus waveguide (FIS single mode fiber smf-28e) and acquiring the transmission spectrum with a conventional InGaAs photodetector (Thorlabs, PDA400) at the other end of the bus waveguide. The coupler in this case is a conventional 50/50 coupler (FIS, SMC 11550229U). The resonances appear as lorentzian-shaped dips in the transmission spectrum and are measured with a linewidth of ~0.08 pm. A change of the pathlength $\Delta l$ that will move one resonant line through one linewidth is $\Delta l=2$ m*0.08 pm/1550 nm~100 nm. The gap length equals $l\pm\Delta l$ where $\Delta l$ is the dimension of the surface feature. The total light path therefore equals the circumference of the ring plus $2d+2(l\pm\Delta l)$. The position of the resonant line can be determined within $\frac{1}{10}^{th}$ of its linewidth and thus the resolution of this device is on the order of $\Delta l=10$ nm.

The sensitivity of the device will increase by reducing the total length L of the resonant structure. If the same device is built with a fiber or waveguide loop of e.g. 2 cm and provided that the linewidth of the resonances remains unchanged, detectable changes of $\Delta l$ would approach 0.1 nm=1 Ångstrom. Ring-resonators that have a smaller pathlength have already been fabricated. Even if such an extraordinary sensitivity is not achieved in practice, it is clear that the invention allows for displacement measurements that are as good as high-resolution interferometers or similar devices.

Data points can be acquired quickly since the wavelength of tunable distributed feedback can be changed/modulated at very high frequency, currently up to GHz frequencies.

Several resonant ring structures of different size L can be multiplexed to one bus waveguide (FIG. 25). It is thus possible to make differential measurements on gap lengths.

It is possible to multiplex several tunable laser sources to one resonant ring structure.

With such an arrangement wavelength dependent parameters of the sample can be determined (FIG. 24).

In another embodiment of the invention, reflective surfaces and or samples before/or bound to a reflective surface can be analyzed with light of different polarization states. Polarization sensitive measurements are possible because the resonant ring structure supports two (or more) orthogonal polarized light modes that appear at distinct resonance frequencies, such as quasi-TE and quasi-TM modes, or corresponding circularly polarized modes.

With reference to FIG. 13, a resonant-ring structure 1102 of total path length L is opened such that the light traverses 'free space' across a gap of length $l_{gap}$. This can be achieved by simple alignment of two optical fibers across an air gap or by using two adjustable lenses (fiber ports—a fiber port consists of an adjustable lens that collimates the light when leaving the fiber; e.g. fiber ports from Optics for Research, NJ) which couples the light in and out of the resonant structure. The resonances are excited by evanescent coupling to a bus waveguide (e.g. using a conventional evanescent wave 50/50 coupler 1110). A tunable source 1104 is coupled into one end of the bus waveguide 1106. A transmission spectrum is collected at the far end of the bus waveguide using a conventional photodetector 1108. The resonance wavelength can be determined from the location of the minimum of lorentzian-shaped dips that appear in the transmission spectrum recorded at the photodetector 1108. In FIG. 13, the total path length $L=l_{wg}+l_{gap}$ where $l_{wg}$ is the length of the waveguide in the ring.

FIG. 16 is a diagram of an embodiment of the present invention employed in a scanning microscope. The light is focused onto the sample surface 1202 using a conventional microscope objective 1122. The surface is scanned by moving either the objective or the sample on a xy stage (raster scanning) 1124.

FIG. 17 is a diagram of a preferred embodiment of the invention as a near field probe for a partially reflecting sample 1204. A tapered optical fiber 1126 with a metal coating is used to create a small aperture. The probe is raster scanned across the sample surface within the near field of the exiting light beam at the tip of the fiber taper 1126.

FIG. 18 is a diagram of a preferred embodiment of the invention as a scanning microscope with an opaque sample similar to a near field optical microscope. The surface of a transparent sample 1206 is scanned with a fiber tip, a tapered fiber tip 1126 or a metal coated tapered fiber tip. The light on the other side of the sample is collected with a conventional objective 1502 and coupled back into the ring structure 1512. The fiber taper 1126 is moved in z-direction (up and down towards the sample surface) with e.g. a piezodrive 1504 at typically kHz frequencies. This size change of the ring resonator 1512 is monitored via detector 1506 from a change of resonance frequencies. Instead of locking into the intensity signal of a conventional NSOM (near field scanning optical microscope) it is now possible to lock into the resonance frequency of the ring resonator. Similar as in an NSOM instrument a surface of the image can be obtained by raster scanning. Any features of the surface will locally change the refractive index of the light path which will lead to an additional shift of the resonance frequency.

FIG. 19 is a diagram of a preferred embodiment of the invention as a scanning microscope. One fiber port 1602 sends a (collimated) beam to an objective 1604. The reflected beam from the sample surface is collected with a second fiber port 1606.

FIG. 20 is a diagram of a preferred embodiment of the present invention for information storage and retrieval. The ring resonator 1712 can scan the height profile of a reflecting surface 1210 with highest precision (nanometer or less) and at high frequencies (Gigahertz) which corresponds to high read rates. A reflecting surface 1210 can thus be used as an information storage device. The height profile encodes information. Each step height of the surface can correspond to a different bit of information or in the case of an analog signal can be converted into a digital format with a suitable converter. Information can be read and possibly written in a similar fashion as in a CD drive. The information density promises to be higher because of the very high resolution of the interferometric ring resonator. Appropriate choice of substrate might even allow one to write information by creation of a height profile from the beam reflected on a primed surface.

FIGS. 21a and b are diagrams of a preferred embodiment of the present invention for distance measurements, pressure strain and vibration measurements. FIG. 21a shows an open ring resonator. The gap is of length $l_{gap}$. Here, the light leaves the waveguiding structure and traverses "free space". Without any external influence such as pressure the gap is of fixed length. FIG. 21b shows how the gap length changes upon external forces due to pressure, temperature, strain, vibrations etc. The gap length changes by a distance Δl. The resonance frequencies of the ring resonator 1812 change accordingly since the total path length $L=l_{wg}+l_{gap}-\Delta l$, where $l_{wg}$ is the length of the waveguide (fiber loop).

FIG. 22 is a diagram of an embodiment of the present invention as a linear (one dimensional) cavity. The resonant ring is replaced with a simple fiber 1912 terminated with mirrors 1902 at both ends. Waveplates or Faraday rotators 1904 can be used to control the state of polarization of this resonant cavity. The gap length is l±Δl where Δl is the change due to temperature, pressure, vibration strain, etc.

FIG. 23 is a diagram of a resonant ring with two inline gaps. The arrangement can be used to determine pressure, temperature, volume or strain that can change the gap distance. In particular it is possible to determine the deflection of an AFM (atomic force microscope) tip (bottom half of FIG. 23). Bending of the AFM cantilever increases the gap distance of a ring resonator located on the cantilever.

FIG. 24 is a diagram of an embodiment of the present invention in which several wavelengths are multiplexed in the same resonant ring. Tunable lasers 1232, 1234, and 1236 have different wavelengths λ1, λ2, and λ3. The tunable lasers 1232, 1234, and 1236 are multiplexed by wavelength multiplexer or coupler 1240 to bus waveguide 1250, which is coupled to ring resonator 1270 by coupler 1260. the bus waveguide 1250 is further connected to wavelength demultiplexer or coupler 1280, which in turn is connected to photodectors 1292, 1294 and 1296. The change of path length Δl can now be determined as a function over a wide spectral range.

FIG. 25 is a diagram of a preferred embodiment of the present invention in which resonant rings of different pathlengths L1, L2, L3 etc. can be multiplexed to the same bus waveguide.

FIG. 26 is a diagram of a preferred embodiment of the invention where the circular waveguide contains a reflecting surface or equivalent structure (dielectric multilayer) and is arranged such that the free space beam is incident onto reflecting surface at an angle. A provision for varying the angle of incidence is shown. An arrangement is shown that contains lenses such that the light that leaves the waveguide is focused onto the reflecting surface (at an angle) and the reflected light is collected with a second lens before it re-enters the resonator. The reflecting surface can be part of a prism or a grating.

FIG. 27 is a diagram of a preferred embodiment of the present invention where the light is incident at an angle onto an SPR metal film 1117 via a prism or equivalent arrangement such that the light excites a surface plasmon resonance. Shown in FIG. 27 is the excitation of a surface plasmon resonance using a Kretschmann configuration. The prism is incorporated in the gap of an open ring-resonator 1115 of total length L between fiber ports 1119 with optional in-line polarizers to change the polarization state of the light incident onto the surface and possibly before the reflected light re-enters the waveguide, here the fiber. Similarly surface plasmon resonances may be excited via an Otto configuration, a grating structure, or a suitable waveguide structure. An analyte binding to the metal surface will change the phase of the SPR and thus the resonance frequencies of the coupled ring resonator. The phase change Δφ occurs only for p-polarized light. Comparing the change of the resonance frequencies Δλ of p versus s polarized light it is possible to perform an internally referenced experiment. Such a sensing device can be used to detect e.g. biomolecular interactions. For this purpose one binding partner, e.g. antibodies, proteins, is immobilized on the metal surface. Binding of the second partner can then be determined from a change of the resonance frequencies of this compound SPR structure. This device can also be used for the detection of viruses, bacteria, DNA and other biological and molecules or samples.

FIGS. 28a and b: Embodiment as in FIG. 27 but with the addition that the surface 1117 may be raster-scanned, such as on an xy stage, to undertake "surface plasmon resonance phase-sensitive imaging" of surfaces. Shown in FIG. 28a is a Kretschmann surface plasmon configuration with prism, metal, glass cover slip (dielectric) that has been coated with a thin metal film (e.g. gold, silver), e.g. 43 nm of gold at 633 nm nominal wavelength, to give rise to a surface plasmon resonance for wavelengths around 630 nm. In addition the surface has been prepared as a checkerboard array 1121 of different biological agents, such as single-stranded DNA, antibodies, or proteins. The biological test sample is introduced onto the surface or flows across the surface due to a fluid flow and any preferential binding (or association) between the surface molecules and the target molecules in solution can be identified from the raster scanned SPR phase image. In FIG. 28b there is shown the configuration where a volume surface plasmon resonance is excited using a fiber tip. The reflected light is collected with the same fiber tip. The fiber tip can be additionally tapered and/or metal coated.

FIG. 29 is a diagram of an embodiment of the present invention as an all-ring SPR coupled resonator. The cladding of part of a fiber loop is removed and metal coated. A SPR resonance is excited in the metal coating at the resonance wavelength of the fiber loop. In an alternative embodiment, a tapered optical fiber 1123 is metal coated and SPR are excited at the resonance wavelengths. An analyte binding to the metal coated fiber can be detected from the phase shift of the SPR measured from the frequency shift of the coupled optical resonator.

FIG. 30 is a diagram of an embodiment similar to that shown in FIG. 29 except that a fiber optic circulator is introduced in the fiber loop. The tip of the fiber 1170 is metal coated so that the light is reflected back through the circulator and a SPR is excited at the optical resonance wavelength. Binding of an anlayte to the metal surface can be measured from a change of optical resonance frequencies. The tip can be tapered very small and can find use as a single cell or single bacteria sensor. The surface of the tip may also be modified for specific detection of DNA (by oligonucleotide immobilization), proteins (e.g. antibody immobilization) etc.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An optical device comprising:
    an optical ring resonator comprising a waveguide, said waveguide having a gap where light beam leaves the waveguide, propagates through a different medium as a traveling wave, and then re-enters the waveguide;
    means for tuning a frequency of a narrow linewidth coherent light source;
    means for coupling light from said light source into said resonator;
    a monitoring system that detects at least one performance parameter of said resonator; and
    a signal processor coupled to said monitoring system to process an output of said ring resonator.

2. An optical device according to claim 1, wherein said optical resonator comprises a fiber-loop resonator, a circular waveguide, a racetrack resonator, a disk resonator, a toroidal resonator, a spherical resonator, or a photonic crystal resonator.

3. An optical device according to claim 1 where said optical resonator comprises at least one reflecting or partially reflecting surface after said gap.

4. An optical device according to claim 3 wherein said reflecting surface is directly deposited on at least a portion of the optical resonator.

5. An optical device according to claim 3 wherein said reflecting surface comprises a metal surface.

6. An optical device according to claim 5 further comprising means for varying the angle of incidence of light incident onto a metallic surface, wherein measurements are performed for different angles of incidence of the light that is incident onto the metal surface.

7. An optical device according to claim 3 wherein said reflecting surface is raster-scanned in a plane normal to said waveguide such that a surface relief of the reflecting surface or a thickness of the reflecting surface, or the optical properties of a sample introduced between the surface and the waveguide is determined.

8. An optical device according to claim 3 wherein an angle of incidence of light onto said reflecting surface changes without changing the overall pathlength of the ring-resonator.

9. An apparatus according to claim 3 further comprising means for varying the angle of incidence of light incident onto a metallic surface, wherein observation and detection are achieved by varying the angle of incidence of light incident onto a metallic surface.

10. An apparatus according to claim 3, further comprising:
    optical elements such that there is a range of angles of incidence; and
    an aperture or iris passed either on the side of the incident or the reflected beam to select part of the light, wherein said aperture is moved in a plane perpendicular to the optic axis allows a portion of the light beam that has a specific angle of incidence to be selected.

11. An optical device according to claim 1 further comprising one of a circulator, polarization optics, or a circulator and polarization optics.

12. An optical device according to claim 1 further comprising a means for delivering a liquid sample wherein said means allows a sample to flow across said gap or said different medium.

13. An optical device according to claim 1 further comprising a photodetector.

14. An optical device according to claim 1 further comprising electronics for control of said light source.

15. An optical device according to claim 14, wherein said electronics further comprises a function generator, a data-acquisition board, and a lock-in amplifier.

16. An optical device according to claim 1 further comprising a sample in said gap or said different medium, said sample comprising one of the following: a liquid, a solid, a gas, a crystal, a thin film, a metallic surface, a dielectric surface, tissue, biological samples viral particles, a polymer and a gel.

17. An optical device according to claim 1 where a path length of said light beam passing through said gap or said different medium changes due to a response of the ring resonator to a physical, chemical or biological change.

18. An optical device according to claim 1 further comprising a plurality of tunable, narrow linewidth coherent light sources multiplexed to said optical resonator.

19. An optical device according to claim 1 wherein said coherent light source operates in a region of an electromagnetic spectrum that permits the observation of resonances.

20. An optical device according to claim 19 wherein said resonances are associated with modes having different states of linear or circular polarization.

21. An optical device according to claim 1 wherein optical components that permit some of the light to be coupled out of the ring resonator have been included in the light path.

22. A method for measuring an optical characteristic comprising the steps of:
    measuring a first value of a property of an output optical signal from an optical resonator at a given position of a sample;
    measuring a second value of the property of the output optical signal from the optical resonator at a different lateral position of the sample; and
    extracting information of the sample from a difference between the first and the second values;
    wherein said property is measured in the presence of a perturbation such that a path-length or phase of said sample located in said optical resonator undergoes a change or is affected such that its optical properties and one or more of its transfer characteristics change with time and are measured.

23. A method for measuring an optical characteristic comprising the steps of:
    measuring a first value of a property of an output optical signal from an optical resonator under at least one of the following conditions: in absence of a sample; at a given position of a sample; for a certain angle of incidence of light onto a sample; and at a given time;
    measuring a second value of the property of the output optical signal from the optical resonator under at least one of the following conditions: when a sample is in an optical path of said optical resonator; at a different lateral position of said sample; a different angle of incidence of light onto a sample; and at a later time;
    extracting information of the sample from a difference between the first and the second values;
    transmitting orthogonal polarization states TE, linear polarization states TM or circular polarization states through a sample or reflecting them from a surface of said sample;
    observing relative frequency shifts or other associated changes in the resonant spectrum of the resonator to detect a difference in the shift of the resonance frequencies for TE versus TM modes; and
    measuring linear or circular birefringence or polarization dependent transmittances of reflectivity.

24. An apparatus for detecting phase changes from a reflected beam at a surface, wherein for polarized light the phase change as well as the reflectivity is different for s-polarized and p-polarized light, comprising:
    an optical ring resonator comprising a waveguide, wherein said waveguide is discontinuous so that a gap is formed where an internally-reflected beam leaves said waveguide, propagates through a sample volume comprising a homogeneous medium or a medium that provides no wave-guiding property by total internal reflection, and then re-enters said waveguide, wherein said resonator experiences relative changes in resonance frequencies of associated modes, said relative changes constituting a measurement;
    means for monitoring properties that change the reflectivity of s- and p-polarized light differently; and
    recording means for recording relative difference in as a function of time allows dynamic processes to be monitored.

* * * * *